(12) United States Patent
Ng et al.

(10) Patent No.: US 11,690,854 B2
(45) Date of Patent: Jul. 4, 2023

(54) METHODS OF TREATING HEAVY MENSTRUAL BLEEDING

(71) Applicant: AbbVie Inc., North Chicago, IL (US)

(72) Inventors: Juki Wing-Keung Ng, Highland Park, IL (US); Mohamad Shebley, North Chicago, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 17/047,871

(22) PCT Filed: Jul. 23, 2018

(86) PCT No.: PCT/US2018/043321
§ 371 (c)(1),
(2) Date: Oct. 15, 2020

(87) PCT Pub. No.: WO2019/203870
PCT Pub. Date: Oct. 24, 2019

(65) Prior Publication Data
US 2021/0154207 A1    May 27, 2021

Related U.S. Application Data

(63) Continuation-in-part of application No. PCT/US2018/028390, filed on Apr. 19, 2018.

(30) Foreign Application Priority Data

Apr. 19, 2018 (WO) ................ PCT/US2018/028390

(51) Int. Cl.
*A61K 31/57* (2006.01)
*A61P 15/00* (2006.01)
(Continued)

(52) U.S. Cl.
CPC ............ *A61K 31/57* (2013.01); *A61K 31/513* (2013.01); *A61K 31/567* (2013.01); *A61P 15/00* (2018.01)

(58) Field of Classification Search
CPC .... A61K 31/57; A61K 31/513; A61K 31/567; A61P 15/00
See application file for complete search history.

(56) References Cited

U.S. PATENT DOCUMENTS 6,225,298 B1   5/2001  Spicer et al.
7,419,983 B2   9/2008  Guo et al.
(Continued)

FOREIGN PATENT DOCUMENTS

WO   WO-0021511 A2 *  4/2000  ............. A61P 15/00
WO       0121194 A2    3/2001
(Continued)

OTHER PUBLICATIONS

Benefetto et al., Expert Opinion on Drug Metabolism & Toxicology, 12:5, 581-588 (Year: 2016).*

(Continued)

*Primary Examiner* — San Ming R Hui
(74) *Attorney, Agent, or Firm* — Neal, Gerber & Eisenberg LLP

(57) ABSTRACT

The present invention relates to the method of treating heavy menstrual bleeding in a subject with or without uterine fibroids and in need of treatment by administering an effective amount of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof, in combination with estrogens and progestogens.

2 Claims, 12 Drawing Sheets

(51) Int. Cl.
A61K 31/513 (2006.01)
A61K 31/567 (2006.01)

(56) References Cited

U.S. PATENT DOCUMENTS

| | | | |
|---|---|---|---|
| 7,700,559 | B2 | 4/2010 | Millar et al. |
| 9,415,085 | B2 | 8/2016 | Van Der Meulen et al. |
| 9,949,974 | B2 | 4/2018 | Goss et al. |
| 10,537,572 | B2 | 1/2020 | Goss et al. |
| 10,682,351 | B2 | 6/2020 | Goss et al. |
| 10,881,659 | B2 | 1/2021 | Chwalisz et al. |
| 11,045,470 | B2 | 6/2021 | Chwalisz et al. |
| 11,344,551 | B2 | 5/2022 | Chwalisz et al. |
| 2009/0280170 | A1 | 11/2009 | Lee et al. |
| 2010/0061976 | A1 | 3/2010 | Ishikawa et al. |
| 2011/0281929 | A1 | 11/2011 | Cuypers et al. |
| 2014/0288031 | A1 | 9/2014 | Chwalisz et al. |
| 2016/0008777 | A1 | 1/2016 | Patel et al. |
| 2016/0339037 | A1 | 11/2016 | Trower |
| 2017/0007600 | A1 | 1/2017 | Gao et al. |
| 2017/0056403 | A1 | 3/2017 | Goss et al. |
| 2018/0163241 | A1 | 6/2018 | Smolke et al. |
| 2019/0054027 | A1 | 2/2019 | Qiu et al. |
| 2019/0054088 | A1 | 2/2019 | Jayanth et al. |
| 2019/0209562 | A1 | 7/2019 | Chwalisz et al. |
| 2020/0163965 | A1 | 5/2020 | Chwalisz et al. |
| 2020/0268752 | A1 | 8/2020 | Goss et al. |
| 2021/0154207 | A1 | 5/2021 | Chwalisz et al. |
| 2021/0275528 | A1 | 9/2021 | Chwalisz et al. |
| 2021/0308135 | A1 | 10/2021 | Shebley |
| 2022/0079945 | A1 | 3/2022 | Chwalisz et al. |

FOREIGN PATENT DOCUMENTS

| | | |
|---|---|---|
| WO | 0155119 A2 | 8/2001 |
| WO | 0121194 A3 | 3/2002 |
| WO | 2005007165 A1 | 1/2005 |
| WO | 2009062087 A1 | 5/2009 |
| WO | 2014143669 A1 | 9/2014 |
| WO | 2016183023 A1 | 11/2016 |
| WO | 2017040841 A1 | 3/2017 |
| WO | 2018060438 A1 | 4/2018 |
| WO | 2018060501 A2 | 4/2018 |
| WO | 2018224497 A1 | 12/2018 |
| WO | 0211732 A1 | 2/2022 |

OTHER PUBLICATIONS

Schwartz et al., Nat Clin Pract Oncol 2007:4;424-432 (Year: 2007).*
Archer et al., Fertility and Sterility, 2017;108(1):152-160 (Year: 2017).*
Bass and Williams, Clinical Pharmacokinetics 15:396-420 (1988) (Year: 1988).*
Verbeeck, Eur J Clin Pharmacol (2008) 64:1147-1161 (Year: 2008).*
Anonymous: "NCT01403038 (v9) submitted on Jan. 4, 2013: A Phase 1, Open-Label Study of the Effects of Elagolix on Ovarian Activity, Ovulation and Ovarian Reserve in Premenopausal Females", Clinicaltrials.gov. [retrieved on Jan. 22, 2020].
Anonymous: "NCT00973973 (v15) submitted on Jan. 2, 2013: A Phase 2, Randomized, Double-Blind, Placebo-Controlled Study to Assess the Efficacy and Safety of NBI-56418 Sodium in Subjects With Endometriosis", Clinicaltrials.gov. [retrieved on Jan. 22, 2020].
Anonymous: "NCT00619866 (v15) submitted on Jan. 2, 2013: A Phase II, Randomized, Double-Blind, Placebo-Controlled Study to Assess the Efficacy and Safety of NBI-56418 in Subjects With Endometriosis", Clinicaltrials.gov. [retrieved on Jan. 22, 2020].
Anonymous: "NCT00437658 (v11) submitted on Jan. 2, 2013: A Phase II, Randomized, Double Blind, Active-controlled Study to Access the Safety and Efficacy of NBI-56418 in Subjects With Endometriosis", Clinicaltrials.gov. [retrieved on Jan. 22, 2020].
Anonymous: "NCT01620528 (v1) submitted on Jun. 13, 2012: A Phase 3, Randomized, Double-Blind, Placebo-Controlled Study to Evaluate the Safety and Efficacy of Elagolix in Subjects With Moderate to Severe Endometriosis-Associated Pain", Clinicaltrials.gov. [retrieved on Jan. 22, 2020].
Anonymous: "NCT01760954 (v1) submitted on Jan. 2, 2013: Extension Study to Evaluate the Long-Term Safety and Efficacy of Elagolix in Subjects With Moderate to Severe Endometriosis-Associated Pain", Clinicaltrials.gov. [retrieved on Jan. 22, 2020].
Anonymous: "NCT01931670 (v1) submitted on Aug. 27, 2013: A Randomized, Double-Blind, Placebo-Controlled Study to Evaluate the Safety and Efficacy of Elagolix in Subjects With Moderate to Severe Endometriosis-Associated Pain", Clinicaltrials.gov. [retrieved on Jan. 22, 2020].
Anonymous: "NCT02143713 (v1) submitted on May 19, 2014: Extension Study to Evaluate the Long-Term Safety and Efficacy of Elagolix in Subjects With Moderate to Severe Endometriosis-Associated Pain", Clinicaltrials.gov. [retrieved on Jan. 22, 2020].
Denny and Mann, Endometriosis-associated dyspareunia: the impact on women's lives, J Fam Plann Reprod Health Care, 33(3):189-193 (2007).
Diamond, M.P., et al., "Elagolix Treatment for Endometriosis-Associated Pain: Results from a Phase 2, Randomized, Double-Blind, Placebo-Controlled Study," Reproductive Sciences, 2014, vol. 21 (3), pp. 363-371.
Carr, B., et al., "Elagolix, an oral GnRH antagonist for endometriosis-associated pain: a randomized controlled study," Journal of Endometriosis and Pelvic Pain Disorders, 2013, vol. 5 (3), pp. 105-115.
Surrey, E., "Long-Term Outcomes of Elagolix in Women With Endometriosis: Results From Two Extension Studies," et al., Obstet Gynecol., vol. 132(1), pp. 147-160.
Archer, D.F., et al., "Elagolix for the management of heavy menstrual bleeding associated with uterine fibroids: results from a phase 2a proof-of-concept study," Fertil Steril. 2017, vol. 108(1), pp. 152-160.
Ng, J., et al., "Dose-Dependent Suppression of Gonadotropins and Ovarian Hormones by Elagolix in Healthy Premenopausal Women," J Clin Endocrinol Metab., 2017, vol. 102(5), pp. 1683-1691.
Kim, S., et al., "Discovery of an Orally Bioavailable Gonadotropin-Releasing Hormone Receptor Antagonist," J Med Chem, 2016, vol. 59(19), pp. 9150-9172.
Anonymous: "NCT01620528 (v20) submitted on Mar. 18, 2017: A Clinical Study to Evaluate the Safety and Efficacy of Elagolix in Subjects With Moderate to Severe Endometriosis-Associated Pain", Clinicaltrials.gov. [retrieved on Dec. 21, 2021].
Anonymous: "NCT01760954 (v18) submitted on Jan. 3, 2018: Study to Evaluate the Long-Term Safety and Efficacy of Elagolix in Subjects With Moderate to Severe Endometriosis-Associated Pain", Clinicaltrials.gov. [retrieved on Dec. 21, 2021].
Anonymous: "NCT01931670 (v21) submitted on Mar. 18, 2017: A Global Phase 3 Study to Evaluate the Safety and Efficacy of Elagolix in Subjects With Moderate to Severe Endometriosis-Associated Pain", Clinicaltrials.gov. [retrieved on Dec. 21, 2021].
Anonymous: "NCT02143713 (v16) submitted on Jan. 3, 2018: Global Study to Evaluate the Long-Term Safety and Efficacy of Elagolix in Subjects With Moderate to Severe Endometriosis-associated Pain", Clinicaltrials.gov. [retrieved on Dec. 21, 2021].
Adamson G.D., "Treatment of Uterine Fibroids: Current Findings With Gonadotropin-releasing Hormone Agonists.," American Journal of Obstetrics and Gynecology, 1992, vol. 166 (2), pp. 746-751.
Anonymous: "NCT01441635 on Sep. 27, 2011: Safety and Efficacy Pre-Menopausal Women With Heavy Uterine Bleeding and Uterine Fibroids", Clinicaltrials.gov Archive, [retrieved on Sep. 27, 2011]. Retrieved from the Internet: URL: http://clinicaltrials.gov/archive/NCT01441635/2011_09_27.
Anonymous: "NCT01441635 on Oct. 5, 2011: Safety and Efficacy Pre-Menopausal Women With Heavy Uterine Bleeding and Uterine Fibroids", Clinicaltrials.gov Archive. [retrieved on Mar. 12, 2015]. Retrieved from the Internet: URL: http://clinicaltrials.gov/archive/NCT01441635/2011_10_05.
Anonymous: "NCT01817530 on Mar. 22, 2013: Safety and Efficacy in Premenopausal Women With Heavy Menstrual Bleeding (HMB) Associated With Uterine Fibroids (UF)", Clinicaltrials.gov Archive,

(56) References Cited

OTHER PUBLICATIONS

[retrieved on Mar. 22, 2013]. Retrieved from the Internet: URL:http://clinicaltrials.gov/archive/NCT01817530/2013_03_22.

ASRM, "Noncontraceptive Benefits of Birth Control Pills" 2011 [retrieved on Mar. 12, 2015]. Retrieved from the Internet: URL: https://www.asrm.org/FACTSHEET_Noncontraceptive_Benefits_of_Birth_Control_Pills/.

Baird D.D., et al., "High Cumulative Incidence of Uterine Leiomyoma In Black and White Women: Ultrasound Evidence.," American Journal of Obstetrics and Gynecology, 2003, vol. 188 (1), pp. 100-107.

Bhatia K., et al., "A Randomised Controlled Trial Comparing GnRH Antagonist Cetrorelix with GnRH agonist Leuprorelin for Endometrial Thinning Prior to Transcervical Resection of Endometrium," BJOG: An International Journal of Obstetrics & Gynaecology, 2008, vol. 115 (10), pp. 1214-1224.

Brown J.S., et al., "Hysterectomy and Urinary Incontinence: A Systematic Review.," Lancet, 2000, vol. 356 (9229), pp. 535-539.

Buttram V.C. Jr., et al., "Uterine Leiomyomata: Etiology, Symptomatology, and Management," Fertility and Sterility, 1981, vol. 36 (4), pp. 433-445.

Cardozo E.R., et al., "The Estimated Annual Cost of Uterine Leiomyomata in the United States.," American Journal of Obstetrics and Gynecology, 2012, vol. 206 (3), pp. e1-9.

Carlson K.J., et al., "The Maine Women's Health Study: I. Outcomes of Hysterectomy.," Obstetrics and Gynecology, 1994, vol. 83 (4), pp. 556-565.

Carr B., et al., "Elagolix, an Oral GnRH Antagonist, Versus Subcutaneous Depot Medroxyprogesterone Acetate for the Treatment of Endometriosis: Effects on Bone Mineral Density," Reproductive sciences, 2014, vol. 21 (11), pp. 1341-1351.

Carr B.R., et al., "An Evaluation of the Effect of Gonadotropin-releasing Hormone Analogs and Medroxyprogesterone Acetate on Uterine Leiomyomata Volume by Magnetic Resonance Imaging: A Prospective, Randomized, Double Blind, Placebo-controlled, Crossover Trial.," The Journal of Clinical Endocrinology and Metabolism, 1993, vol. 76 (5), pp. 1217-1223.

Chwalisz K., et al., "Selective Progesterone Receptor Modulator Development and use In the Treatment of Leiomyomata and Endometriosis.," Endocrine Reviews, 2005, vol. 26 (3), pp. 423-438.

Daniels A., et al., "Treatment with the Gnrh Agonist (gnrha) Desorelin (d) and Low-dose Add-back Estradiol (e2) is Effective in Reducing Pain, Bleeding, and Uterine Volume (uv) while Maintaining Bmd In Women with Symptomatic Uterine Fibroids (uf).," Fertility and Sterility, 2002, vol. 78 (3 Suppl 1), pp. S65-S66.

Ehlers K., et al., Global Library of Women's Medicine, 2013, ISSN: 1756-2228.

Extended European Search Report for Application No. EP18171240, dated Sep. 6, 2018, 5 pages.

FDA Approves Lysteda to Treat Heavy Menstrual Bleeding Silver Spring, MD; US Food and Drug Administration, Nov. 13, 2009. Reterived from http://www.fda.gov/NewsEvents/Newsroom/PressAnnouncements/ucm 190551.htm.

Felberbaum R.E., et al., "Treatment of Uterine Fibroids with a Slow-release Formulation of the Gonadotrophin Releasing Hormone Antagonist Cetrorelix," Human Reproduction, 1998, vol. 13 (6), pp. 1660-1668.

Felberbaum R.E., et al., "Will GnRH Antagonists Assist in the Treatment of Benign Gynaecological Diseases?," Reproductive BioMedicine Online, 2002, vol. 5, pp. 68-72.

Friedman A.J., et al., "A Prospective, Randomized Trial of Gonadotropin-releasing Hormone Agonist Plus Estrogen-progestin or Progestin "add-back" Regimens for Women With Leiomyomata Uteri.," The Journal of Clinical Endocrinology and Metabolism, 1993, vol. 76 (6), pp. 1439-1445.

Hallberg L., et al., "Determination of Menstrual Blood Loss," Scandinavian Journal of Clinical and Laboratory Investigation, 1964, vol. 16, pp. 244-248.

Hendrix S.L., "Bilateral Oophorectomy and Premature Menopause.," The American Journal of Medicine, 2005, vol. 118 (Suppl 12B), pp. 131-135.

Hickey M., et al., "Superficial Endometrial Vascular Fragility In Norplant Users and In Women With Ovulatory Dysfunctional Uterine Bleeding.," Human Reproduction, 2000, vol. 15 (7), pp. 1509-1514.

International Search Report and Written Opinion for Application No. PCT/US2014/027673, dated May 27, 2014, 10 pages.

International Search Report and Written Opinion for Application No. PCT/US2018/043321, dated Oct. 30, 2018, 9 pages.

International Search Report and Written Opinion for Application No. PCT/US2018/28390, dated Aug. 8, 2018, 17 pages.

Kupker W., et al., "Use of GnRH Antagonists in the Treatments of Endometriosis," Reproductive BioMedicine Online, 2002, vol. 5(1), pp. 12-16.

Lethaby A., et al., "Pre-operative Gnrh Analogue therapy Before Hysterectomy or Myomectomy for Uterine Fibroids.," The Cochrane Database of Systematic Reviews, 2009, vol. 1, pp. 1-97.

Maresh M.J., et al.,"The Value National Hysterectomy Study: Description of the Patients and their Surgery.," BJOG , 2002, vol. 109 (3), pp. 302-312.

Maruo T., et al., "Effects of Progesterone on Uterine Leiomyoma Growth and Apoptosis.," Steroids, 2000, vol. 65 (10-11), pp. 585-592.

Myers E.R., et al., "Management of Uterine Leiomyomata: What Do We Really Know?," Obstetrics and Gynecology, 2002, vol. 100(1), pp. 8-17.

NCT00797225 (published Feb. 6, 2012) (Year: 2012).

North American Menopause Society, "Treatment of Menopause-associated Vasomotor Symptoms: Position Statement of the North American Menopause Society.," Menopause, 2004, vol. 11 (1), pp. 11-33.

Sabry M., et al., "Innovative Oral Treatments of Uterine Leiomyoma," Obstetrics and Gynecology International, 2012, vol. 30 (1), pp. 1-10.

Sabry M., et al., "Medical Treatment of Uterine Leiomyoma," Reproductive Sciences, 2012, vol. 19 (4), pp. 339-353.

Simbar M., et al., "A Three-dimensional Study of Endometrial Microvessels In Women Using the Contraceptive Subdermal Levonorgestrel Implant System, Norplant.," Micron, 2004, vol. 35 (7), pp. 589-595.

Stewart A., et al., "The Effectiveness of the Levonorgestrel-releasing Intrauterine System In Menorrhagia: A Systematic Review.," BJOG , 2001, vol. 108 (1), pp. 74-86.

Stewart E.A., "Uterine Fibroids.," Lancet, 2001, vol. 357 (9252), pp. 293-298.

Stovall T.G., "Gonadotropin-releasing Hormone Agonists: Utilization Before Hysterectomy.," Clinical Obstetrics and Gynecology, 1993, vol. 36 (3), pp. 642-649.

Struthers R.S. et al., "Suppression of Gonadotropins and Estradiol in Premenopausal Women by Oral Administration of the Nonpeptide Gonadotropin-Releasing Hormone Antagonist Elagolix," The Journal of Clinical Endocrinology & Metabolism, 2009, vol. 94 (2), pp. 545-551.

Supplementary European Search Report for Application No. EP14717031, dated Sep. 23, 2015, 4 pages.

Supplementary International Search Report for Application No. PCT/US2014/027673, dated Dec. 19, 2014, 5 pages.

Surrey E.S., "Steroidal and Nonsteroidal "Add-back" Therapy: Extending Safety and Efficacy of Gonadotropin-Releasing Hormone Agonists in the Gynecologic Patient," Fertility and Sterility, 1995, vol. 64 (4), pp. 673-685 (abstract).

Taylor H.S., et al., "Treatment of Endometriosis-Associated Pain with Elagolix, an Oral GnRH Antagonist," The New England Journal of Medicine, 2017, vol. 377, pp. 28-40.

The Menorrhagia Research Group, "Quantification of Menstrual Blood Loss.," The Obstetrician & Gynaecologist., 2004, vol. 6, pp. 88-92.

Tiltman A.J., "The Effect of Progestins on the Mitotic Activity of Uterine Fibromyomas.," International Journal of Gynecological Pathology, 1985, vol. 4 (2), pp. 89-96.

(56) References Cited

OTHER PUBLICATIONS

Welsh A, Heavy Menstrual Bleeding, ed. London: RCOG Press at Royal College of Obstetricians and Gynaecologists; 2007.
International Search Report and Written Opinion for Application No. PCT/US2019/44613, dated Oct. 25, 2019, 27 pages.
Anonymous: "NCT00797225 (v15) submitted on Jan. 2, 2013: A Phase II, Randomized, Double-Blind, Placebo- and Active-Controlled Study to Assess the Efficacy and Safety of NBI-56418 in Subjects With Endometriosis", Clinicaltrials.gov. [retrieved on Jan. 22, 2020].
AbbVie Inc., Prescribing Information for Orilissa (elagolix), revised Jul. 2018, 34 pages.
Eocco., "Elagolix Pharmacy Coverage Policy," Retrieved online [Aug. 4, 2022], Retrieved from the Internet: URL: https://www.eocco.com/-/media/EOCCO/PDFs/Formulary/elagolix_orilissa.pdf.
Harding G., et al., "The Responsiveness of the Uterine Fibroid Symptom and Health-related Quality of Life Questionnaire (UFS-QOL)," Health and Quality of Life Outcomes, 2008, vol. 6 (1), pp. 1-8.
Ma X., et al., "Comparison of the Spine and Hip BMD Assessments Derived from Quantitative Computed Tomography," International Journal of Endocrinology, 2015, vol. 2015, 5 pages.
Tafi E., et al., "Advances in Pharmacotherapy for Treating Endometriosis," Expert Opinion on Pharmacotherapy, 2015, vol. 16(16), pp. 2465-2483.
Anonymous: "NCT00437658 (v10) submitted on Mar. 6, 2012: A Phase II, Randomized, Double Blind, Active-controlled Study to Access the Safety and Efficacy of NBI-56418 in Subjects with Endometriosis", Clinicaltrials.gov, [retrieved on Sep. 28, 2022].
Anonymous: "NCT00797225 (v14) submitted on Feb. 6, 2012: Efficacy and Safety Study in Endometriosis with NBI-56418; Placebo and Active Controlled", Clinicaltrials.gov, [retrieved on Sep. 16, 2022].
Anonymous: "NCT00979973 (v14) submitted on Feb. 6, 2012: Efficacy and Safety Study of NBI-56419 Sodium in Subjects with Endometriosis", Clinicaltrials.gov, [retrieved on Sep. 28, 2022].
Anonymous: "NCT01403038 (v4) submitted on Nov. 4, 2011: An Open-label Study of the Effects of Elagolix in Adult Premenopausal Females", Clinicaltrials.gov, [retrieved on Sep. 28, 2022].
Anonymous: "NCT01441635 (v9) submitted on Jan. 3, 2013: Safety and Efficacy Pre-Menopausal Women With Heavy Uterine Bleeding and Uterine Fibroids", Clinicaltrials.gov, [retrieved on Sep. 29, 2022].
Anonymous: "NCT01620528 (v4) submitted on Jan. 2, 2013: A Clinical Study to Evaluate the Safety and Efficacy of Elagolix in Subjects with Moderate to Severe Endometriosis-Associated Pain", Clinicaltrials.gov, [retrieved on Sep. 29, 2022].
Carr et al., Fertility and Sterility, 96(3), S45, 2011.
Chen et al., J. Med. Chem. 51, 7478-7485, 2008.
Deal Watch: Abbott and Neurocrine to develop promising endometriosis drug, Nature Reviews Drug Discovery, 9, 584, 2010.
DiMasi et al., Clinical Pharmacology & Therapeutics, 87(3), 272-277, 2010.
European Medicines Agency, ICH Topic E 4—Dose Response Information to Support Drug Registration (CPMP-ICH-378-95) dated Nov. 1994, 10 pages.
Eurpoean Medicines Agency, Committee for Medicinal Products for Human Use (CHMP) (EMEA/CHMP/SWP28367/07) dated Jul. 2007, 12 pages.
Imani et al., Fertility and Sterility, 92(3), S111-S112, 2009.
Napodano, Jason, Zacks Small-Cap Research for Neurocrine Biosciences, Inc. dated Oct. 5, 2011, 11 pages.
Neurocrine Biosciences, Inc. Press Release dated Dec. 10, 2009, 3 pages.
Neurocrine Biosciences, Inc. Press Release dated Jul. 29, 2009, 2 pages.
Neurocrine Biosciences, Inc. Press Release dated May 24, 2010, 2 pages.
Neurocrine Biosciences, Inc. Press Release dated Nov. 22, 2010, 2 pages.
Neurocrine Biosciences, Inc. Press Release dated Sep. 2, 2008, 1 page.
Novo Nordisk Inc., Activella Physician Insert dated Dec. 2006, 37 pages.
Riggs et al., CPT: Pharmacometrics & Systems Pharmacology, 1, e11, 2012.
Riggs et al., poster at American Conference on Pharmacometrics, San Diego, CA, Apr. 3-7, 2011.
Rowland and Tozer, Clinical Pharmacokinetics: Concepts and Applications, 3rd ed., Lippincott Williams & Wilkins, 83-105, 1995.
Thornber, Chemical Society Reviews, 8, 563-580, 1979.
United States Securities and Exchange Commission, Neurocrine Biosciences Inc. Form 10-K submitted on Feb. 10, 2011, 91 pages.
Asha et al., The Journal of Obstetric and Gynecology of India, May/Jun. 2011, 301-306.
Gatongi et al., The Obstetrician & Gynaecologist, 7, 75-79, 2005.
Borcherding et al., Arch Inter Med, 152, 711-716, 1992.
Chwalisz et al., Reproductive Sciences, 19(6), 563-571, 2012.

* cited by examiner

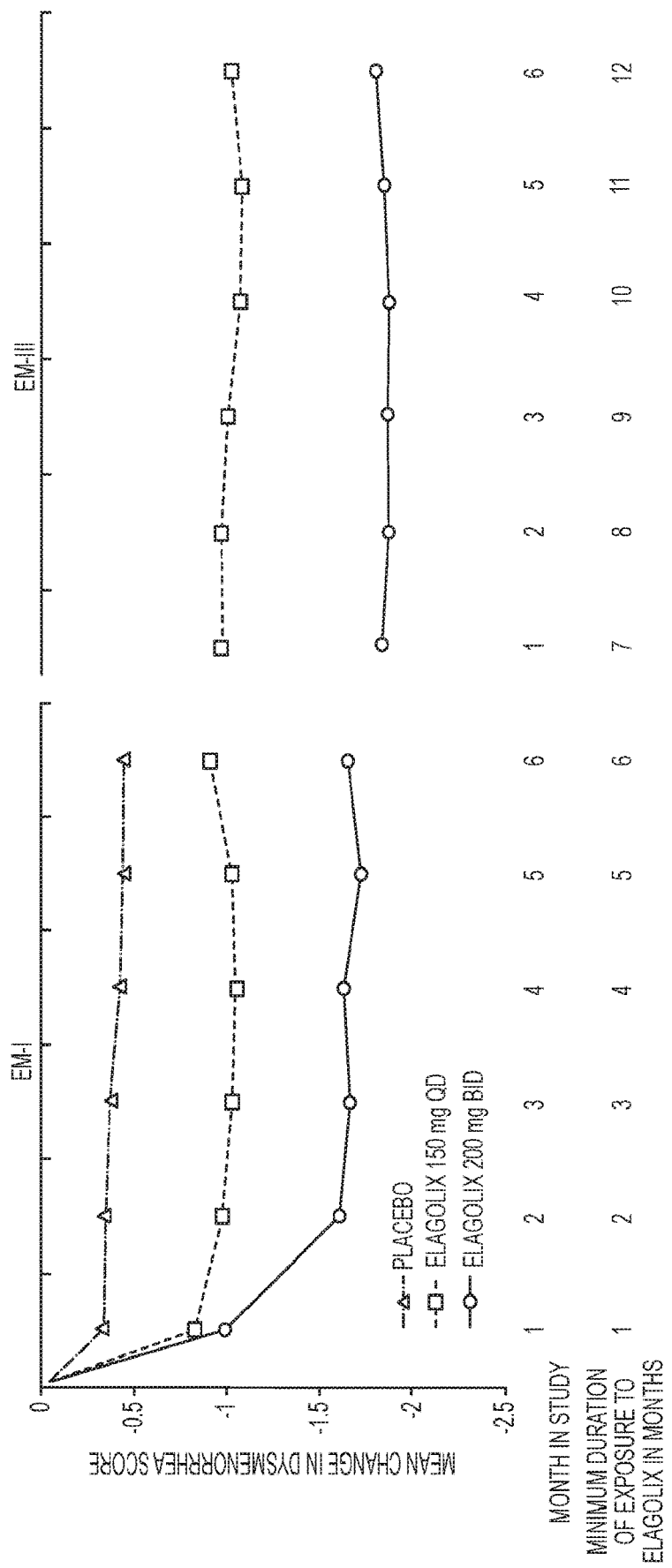
FIGURE A-1

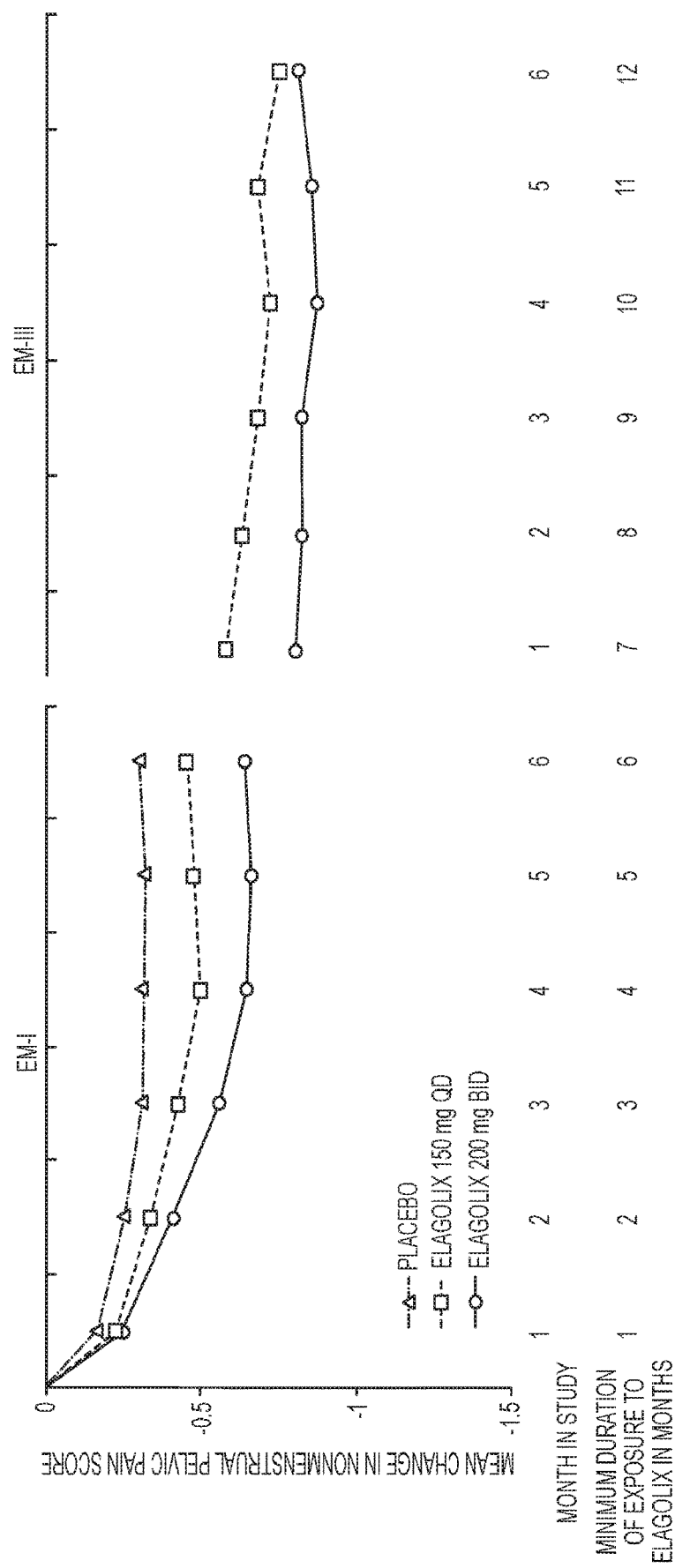
FIGURE A-2

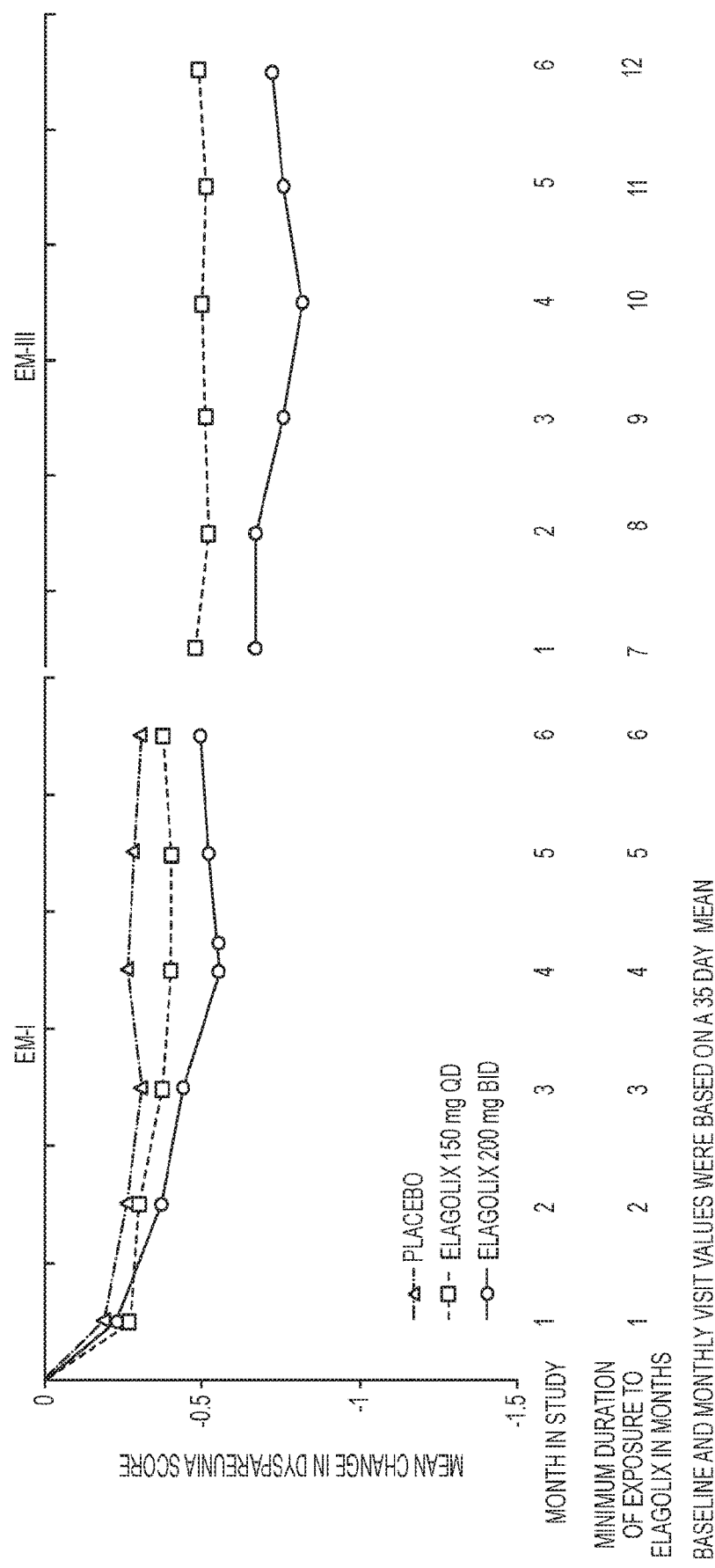
FIGURE A-3

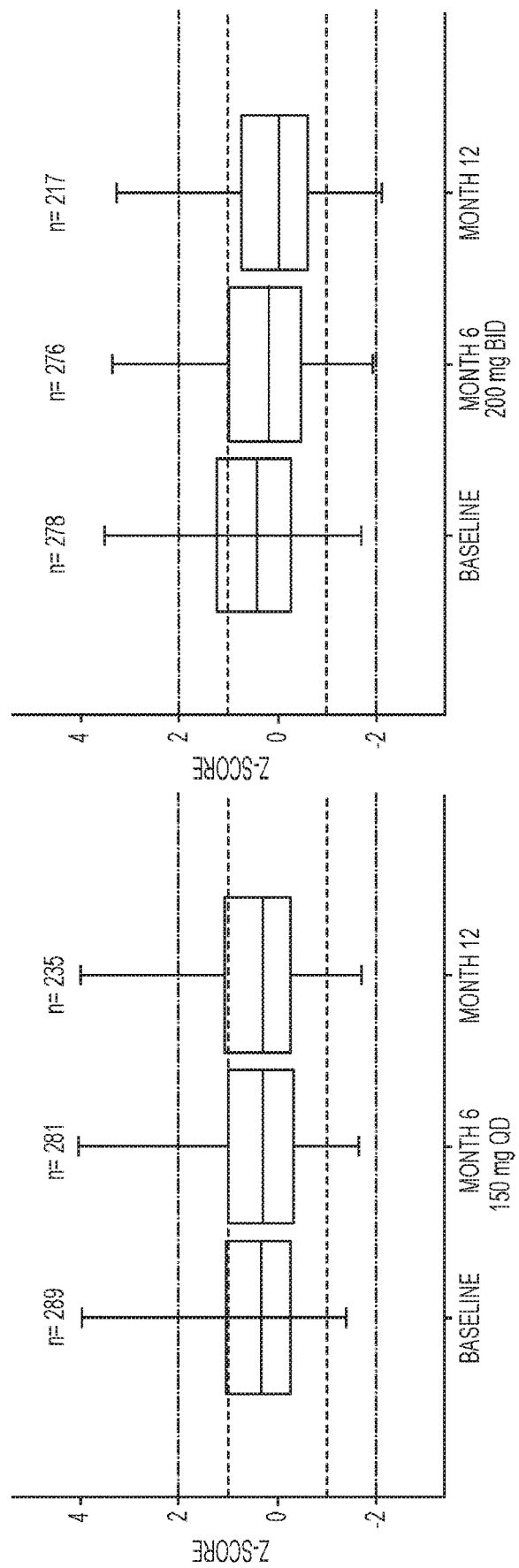
FIGURE A-4

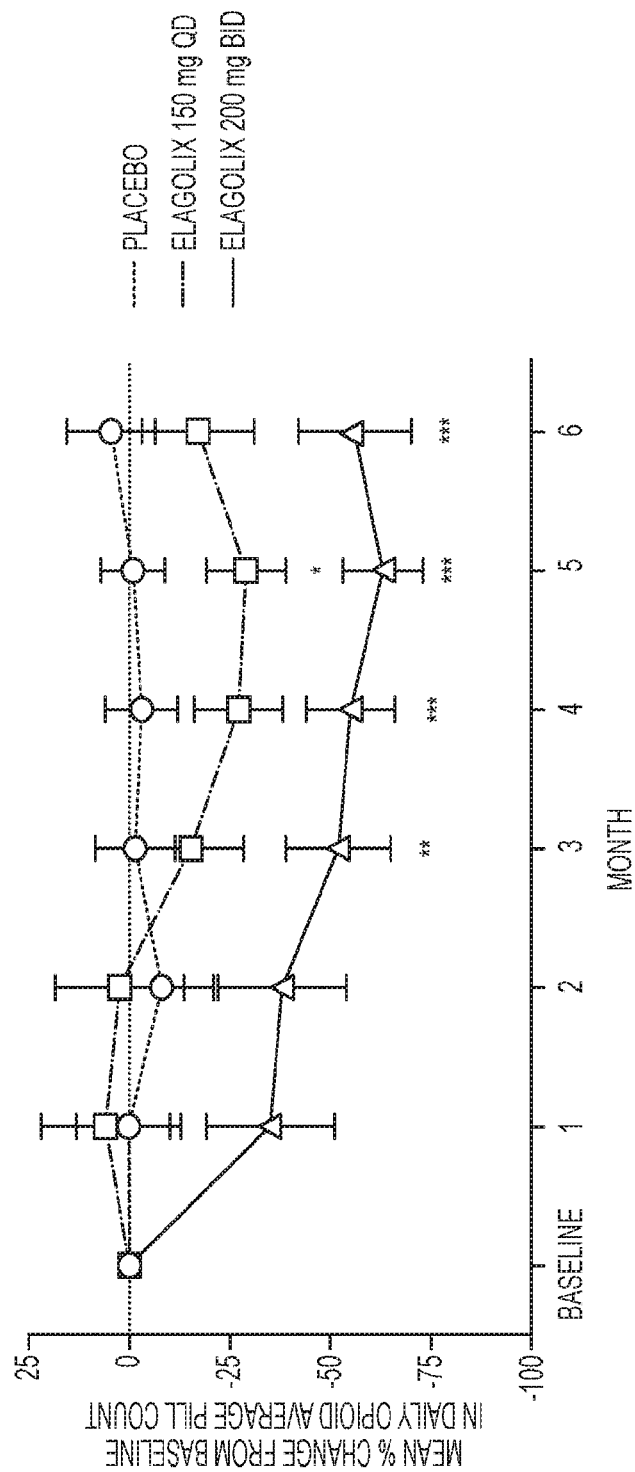
FIGURE A-5

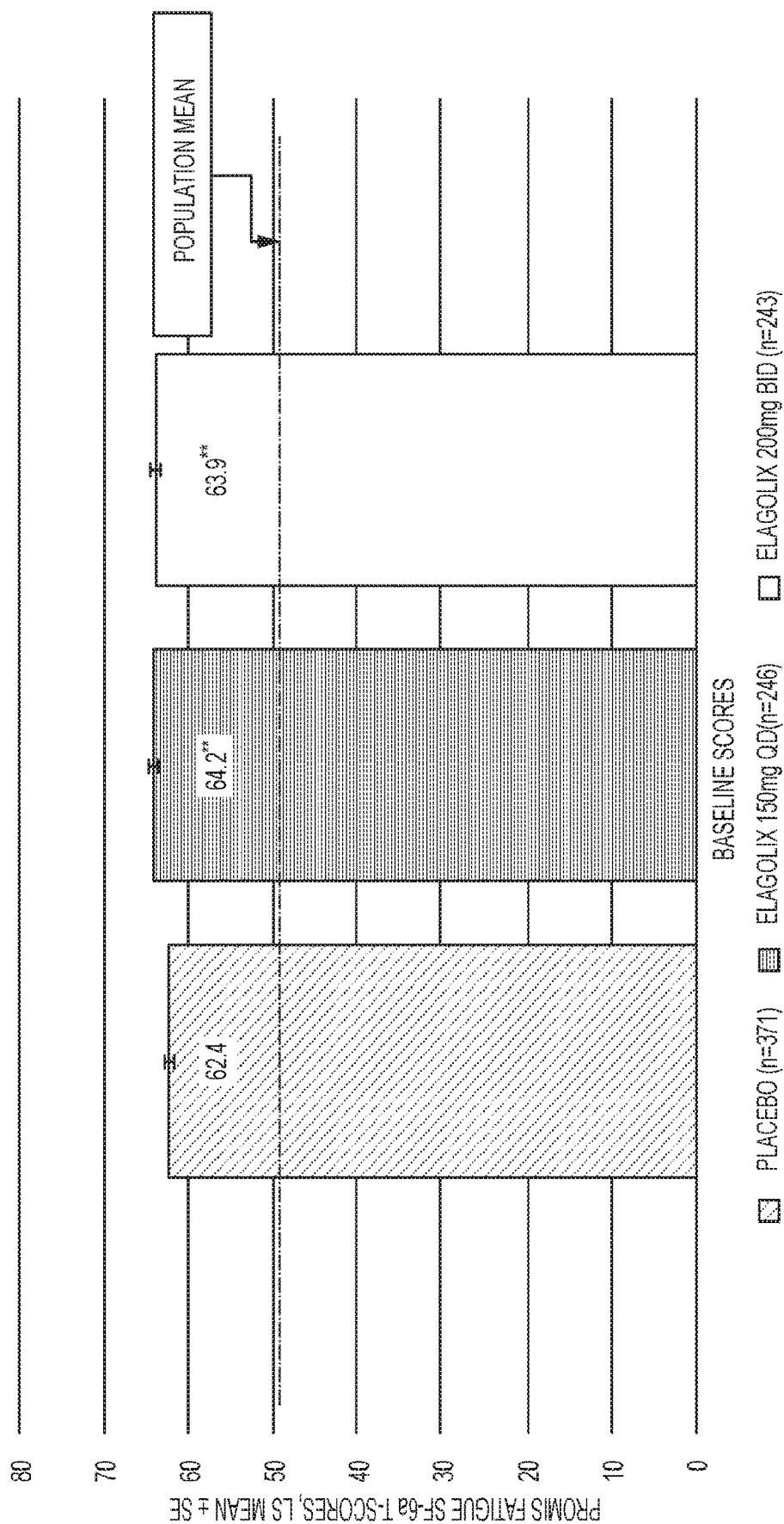
FIGURE A-6

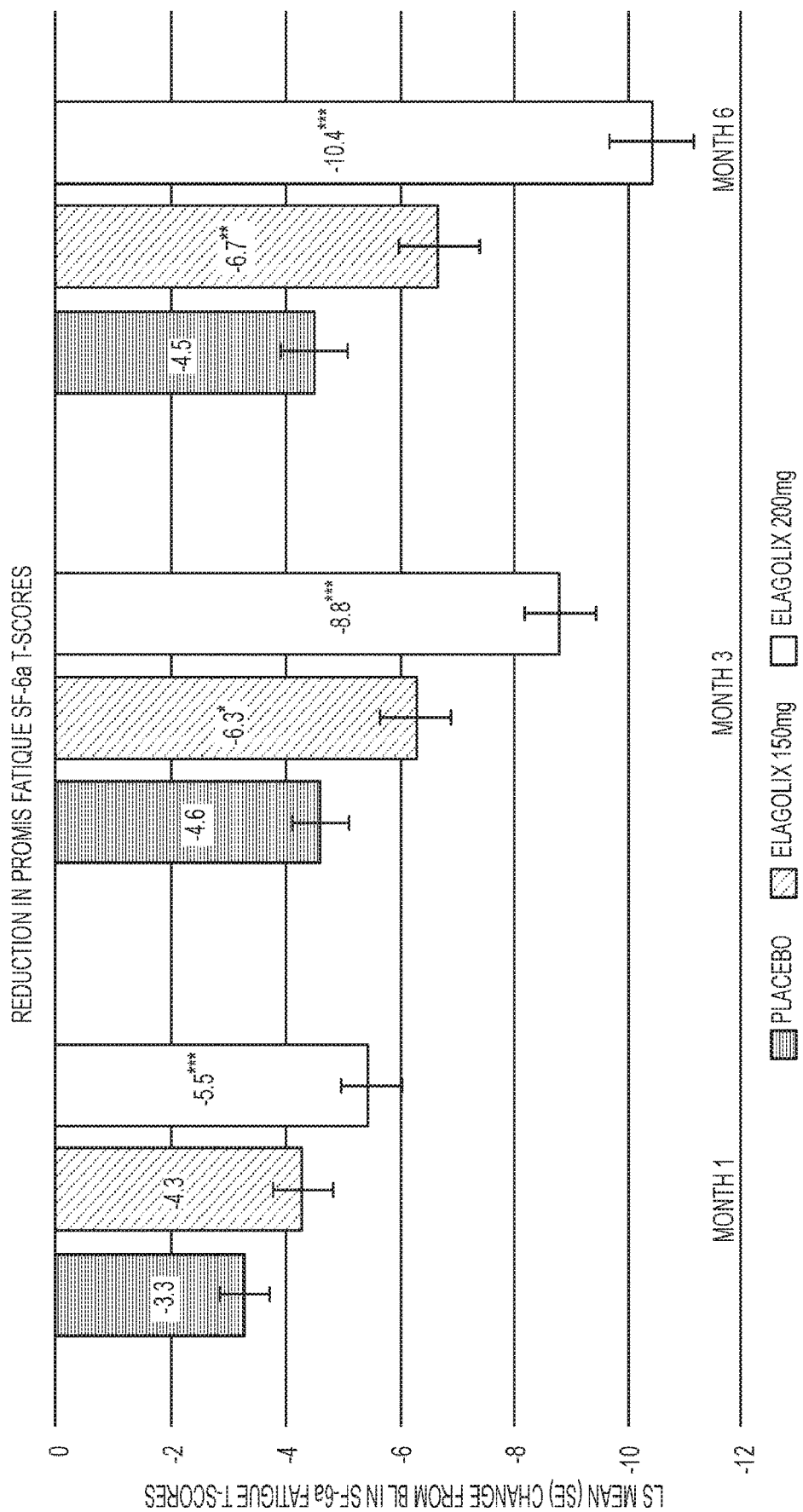
FIGURE A-7

METHODS OF TREATING HEAVY MENSTRUAL BLEEDING

CROSS REFERENCE TO RELATED APPLICATIONS

This patent is a National Stage Entry of International Application Number PCT/US2018/043321, filed on Jul. 23, 2018, which is a continuation-in-part of and seeks priority from non-provisional application PCT/US2018/028390, filed on Apr. 19, 2018; the entire contents of which applications are fully incorporated herein by reference.

FIELD OF THE INVENTION

This invention pertains to the use of GnRH receptor antagonists for the treatment of heavy menstrual bleeding in a subject with or without uterine fibroids.

BACKGROUND OF THE INVENTION

Endometriosis is a disease in which tissue normally found in the uterine cavity (i.e., endometrium) is found outside the uterus, usually implanted on the peritoneal lining of the pelvis. Endometriosis affects an estimated 1 in 10 women of reproductive age and can cause pain, infertility, and sexual dysfunction. Growth of endometrial tissue outside of the uterine cavity is believed to be estrogen-dependent. Thus, current therapies for endometriosis are aimed at altering estrogen levels.

Uterine fibroids (leiomyomas) are benign tumors and are highly prevalent in women of reproductive age. Symptoms associated with uterine fibroids most commonly include heavy or prolonged menstrual bleeding, pelvic pressure and pelvic organ compression, back pain, and adverse reproductive outcomes. Heavy menstrual bleeding (HMB; menorrhagia, defined as greater than 80 mL per menstrual cycle) (The Menorrhagia Research Group. Quantification of menstrual blood loss. The Obstetrician & Gynaecologist. 2004; 6:88-92) is inconvenient and may lead to iron-deficiency anemia, which is the leading cause of surgical interventions that may include hysterectomy. Other symptoms, in particular pressure symptoms, are largely dependent on the size, number, and location of the tumors.

Although the pathogenesis has yet to be fully elucidated, the growth of uterine fibroids is known to be highly dependent on both estrogen and progestogen. Fibroids tend to shrink after menopause due to a decrease in hormone production. On this basis, most medical treatments for women with symptomatic uterine fibroids are aimed at either hormone-blocking or hormone-modulating strategies.

Adenomyosis is a condition in which the inner lining of the uterus (the endometrium) breaks through the muscle wall of the uterus (the myometrium). Adenomyosis can cause menstrual cramps, lower abdominal pressure, and bloating before menstrual periods and can result in heavy periods. The condition can be located throughout the entire uterus or localized in one spot. Adenomyosis is a common condition. It is most often diagnosed in middle-aged women and women who have had children. Some studies also suggest that women who have had prior uterine surgery may be at risk for adenomyosis.

Polycystic ovary syndrome (PCOS) is a hormonal disorder common among women of reproductive age. Women with PCOS may have infrequent or prolonged menstrual periods or excess male hormone (androgen) levels. The ovaries may develop numerous small collections of fluid (follicles) and fail to regularly release eggs.

Gonadotropin-releasing hormone (GnRH) is a peptide that stimulates the secretion of the pituitary hormones that are responsible for sex steroid production and normal reproductive function. GnRH agonists are used to treat endometriosis, uterine fibroids or adenomyosis by suppressing the activity of the pituitary-gonadal axis. However, GnRH agonists cause an initial stimulation of gonadotropic and gonadal hormones, such as estrogen.

Peptide GnRH antagonists competitively bind to GnRH receptors in the pituitary gland, blocking the release of gonadotropins, such as luteinizing hormone (LH) and follicle-stimulating hormone (FSH) from the pituitary. Such peptide GnRH antagonists have been approved for oncology and assisted reproduction. However, administration is inconvenient, with peptide GnRH antagonists being delivered as daily subcutaneous injections or as long-acting depot formulations.

Thus, there is a need in the art for new orally administered treatments for endometriosis, uterine fibroids, adenomyosis and polycystic ovary syndrome, and, in particular, management of pain associated with endometriosis or adenomyosis and heavy menstrual bleeding associated with uterine fibroids or adenomyosis. Moreover, there remains a need in the art to develop orally bioavailable dosage forms comprising such treatments and, in particular, a nonpeptide GnRH antagonist.

BRIEF SUMMARY OF THE INVENTION

The invention generally provides a method of treating endometriosis associated pain wherein the method further reduces fatigue in patients with moderate to severe endometriosis, or wherein the method further reduces use of pain medications in patients with moderate to severe endometriosis. In this method the treatment comprises administering 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof. In one embodiment, Compound A or its pharmaceutically acceptable salt is administered in combination with estrogens and progestogens. The estrogen is selected from the group consisting of estradiol, ethinyl estradiol, and conjugated estrogens. The progestogen is selected from the group consisting of progesterone, norethindrone acetate, norgestimate, drospirenone, and medroxyprogesterone. Preferably, the estrogen is estradiol and the progestogen is norethindrone acetate.

In one embodiment, the estradiol is administered in an amount of about 0.5 mg and the norethindrone acetate is administered in an amount of about 0.1 mg per day. In this embodiment, the estradiol and norethindrone acetate are administered once per day.

In yet another embodiment, the estradiol is administered in an amount of about 1.0 mg and the norethindrone acetate is administered in an amount of about 0.5 mg per day. In this embodiment, the estradiol and norethindrone acetate are administered once per day.

In one aspect of the invention, the estradiol is administered continuously and norethindrone acetate are administered once per day during the last 12-14 days of a menstrual cycle.

In yet another embodiment, the Compound A is dosed 150 mg once-a-day, 200 mg twice-a-day, 300 mg twice-a-day or 600 mg once-a-day.

Therefore, in one embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 300 mg per day. In another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 150 mg per day. 300 mg of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof may be dosed twice a day. 150 mg of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof may also be dosed twice-a-day.

In another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 400 mg per day. In yet another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 200 mg per day.

400 mg of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof may also be dosed twice-a-day. 200 mg of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof may also be dosed twice-a-day.

In yet another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 600 mg per day. Further, in another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In another aspect of the invention, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 28 days. In yet another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 56 days. In another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 84 days. And, in yet another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 168 days. Further, in another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for about 168 days to about 1 year.

Preferably, in different aspects of the invention, the estrogen is estradiol and the progestogen is progesterone. In another embodiment, the estradiol is administered continuously and the progesterone is administered once per day during the last 12-14 days of a menstrual cycle.

In another aspect, the present invention provides a method of treating endometriosis, the method comprising administering to a patient in need thereof 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof, wherein said patient experiences bone mineral density loss, wherein the bone mineral density loss is substantially reversed upon discontinuation of Compound A, or pharmaceutically acceptable salt thereof.

In yet another aspect, the present invention provides for administering to a patient in need thereof 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof, wherein said patient experiences bone mineral density loss, wherein the bone mineral density loss is substantially reversed upon discontinuation of Compound A, or pharmaceutically acceptable salt thereof.

The present invention relates to methods for reducing the volume of menstrual blood loss in a subject with or without uterine fibroids. The present invention also relates to a method for reducing the fibroid and uterine volume and treatment for non-bleeding-related symptoms of uterine fibroids. The methods comprise administering to a subject 300 to 600 mg per day of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof, in combination with estrogens and progestogens. In the above methods, the estrogen is selected from the group consisting of estradiol, ethinyl estradiol, and conjugated estrogens, and the progestogen is selected from the group consisting of progesterone, norethindrone acetate, norgestimate, drospirenone, and medroxyprogesterone. For example, in the above methods, the estrogen is estradiol and the progestogens are norethindrone acetate and progesterone.

Subjects in need of treatment thereof have a volume of menstrual blood greater than 80 mL per menstrual cycle. Once said subjects are treated according to the above methods, these subjects have a volume of menstrual blood loss that is less than 80 mL per menstrual cycle.

Subjects treated according to the above methods can have uterine fibroids or do not have uterine fibroids.

Subjects treated according to the above methods can have non-bleeding symptoms related to uterine fibroids ("bulk symptoms") such as pelvic pressure, bloating, pelvic pain, urinary problems, etc.

In the above methods, the estradiol and norethindrone acetate (which is a progestogen) are administered orally once per day. For example, in one aspect, the estradiol is administered in an amount of about 0.5 mg and the norethindrone acetate is administered in an amount of about 0.1 mg per day. In another aspect, the estradiol is administered in an amount of about 1.0 mg and the norethindrone acetate is administered in an amount of about 0.5 mg per day. Alternatively, the estradiol is administered continuously and the norethindrone acetate is administered once per day during the last 12-14 days of a menstrual cycle.

In the above methods, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 300 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above methods, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 400 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above methods, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 600 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above methods, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 28 days. In another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 56 days. In yet still another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 84 days. In still yet another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 168 days. In still yet another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for about 168 days to about 1 year.

The present invention also relates to a method for treating uterine fibroids in a subject in need of treatment. The method comprises administering to the subject 300 to 600 mg per day of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof, in combination with estrogens and progestogens. For example, in the above method, the estrogen is estradiol and the progestogens are norethindrone acetate and progesterone.

In the above method, the estradiol and norethindrone acetate are administered once per day. For example, in one aspect, the estradiol is administered in an amount of about 0.5 mg and the norethindrone acetate is administered in an amount of about 0.1 mg per day. In another aspect, the estradiol is administered in an amount of about 1.0 mg and the norethindrone acetate is administered in an amount of about 0.5 mg per day.

In the above method, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 300 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above method, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 400 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above method, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 600 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above method, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 28 days. In another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 56 days. In yet still another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 84 days. In still yet another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 168 days. In still yet another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for about 168 days to about 1 year.

The invention further provides in one embodiment, a method of reducing fatigue or pain medications in a patient wherein the patient is diagnosed with a condition selected from a group consisting of Uterine Fibroids, Endometriosis, Adenomyosis or Polycystic Ovary Syndrome, the method comprising administering to 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof, wherein fatigue is reduced in said patient or wherein pain medications is reduced to said patient. In one aspect of the patient is diagnosed with a condition selected from a group consisting of Uterine Fibroids, Endometriosis, Adenomyosis or Polycystic Ovary Syndrome. In one embodiment, the patient is diagnosed with Uterine Fibroids. In another embodiment the patient is diagnosed with Endometriosis. In one embodiment the patient is diagnosed with Adenomyosis. In one embodiment the patient is diagnosed with Polycystic Ovary Syndrome.

BRIEF DESCRIPTION OF THE FIGURES

FIG. 1 shows the last observation carried forward (LOCF) for the last 28 days of treatment in all subjects. The composite bleeding endpoint shown on the left was calculated using alkaline hematin data. Amenorrhea was calculated using both alkaline hematin data and a daily bleeding diary data. For each of the Composite Bleeding Endpoint and Amenorrhea bar graphs shown in FIG. 1, patients were treated with Elagolix 300 BID (N=30) (first bar on the far left), E600 QD (N=28) (second bar from the left), E300+estrogen (1.0 mg of estradiol (Estrace®)) and 200 mg progesterone (cyclical Prometrium®) (collectively referred to as "EP") (N=26) (third bar rom the left), E200 BID (N=33) (fourth bar from the left), E400 QD (N=31) (fifth bar from the left), E200 BID+a low dose Activella® (a combination of 0.5 mg estradiol and 0.1 mg northindrone acetate) (referred to as "A") (N=34) (sixth bar from the left), E100 BID (seventh bar from the left) (N=31) and placebo (PBO) (N=49) (eighth bar from the left (or first on the right)). P values are defined as: *p<0.001 for Elagolix vs. pooled placebo (PBO; PBO from cohorts 1, 2 & 4). p<0.01 for Elagolix vs. pooled PBO (PBO from cohorts 1, 2 & 4).

Figure 1:
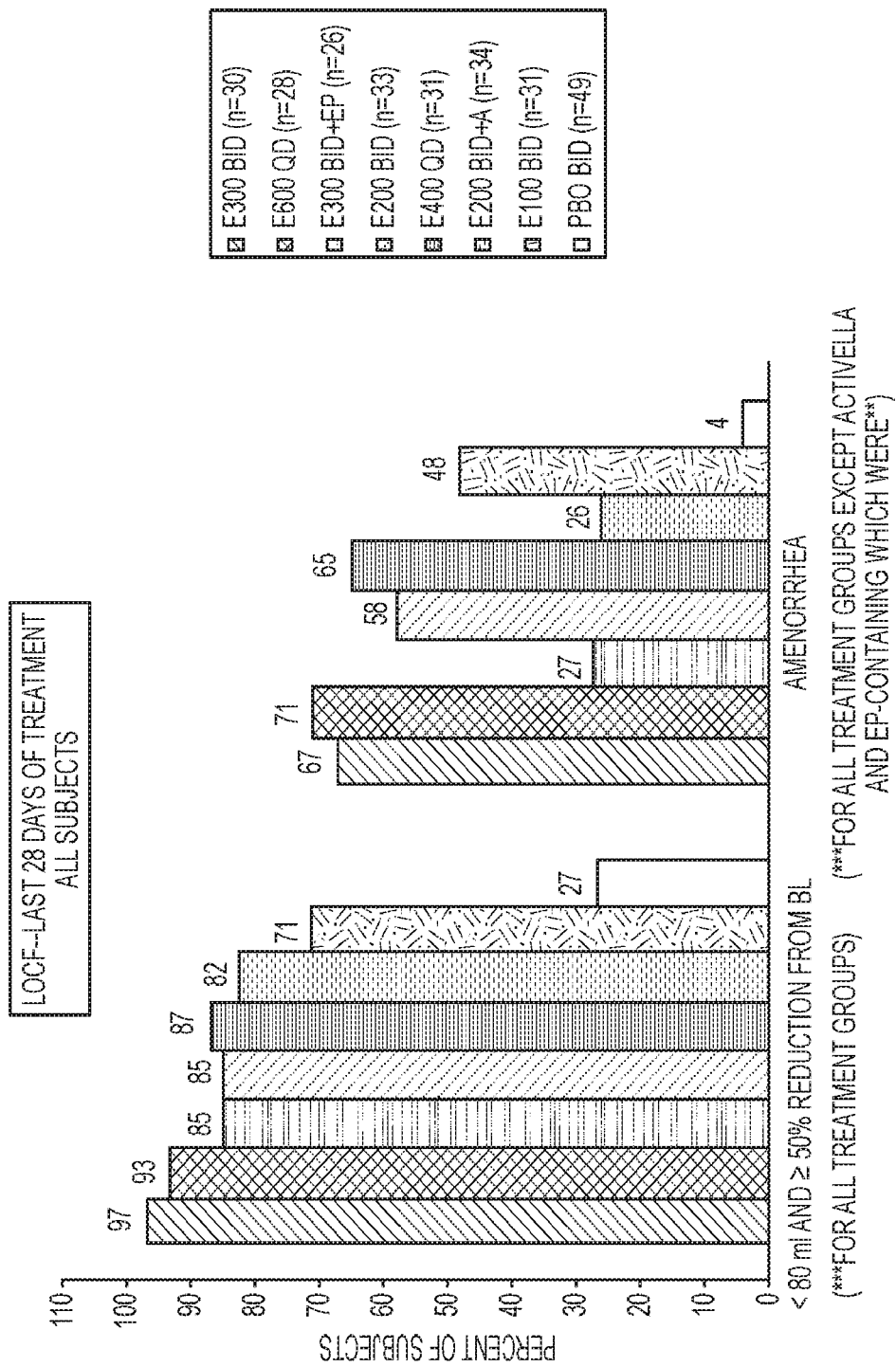
FIG. 1 shows the composite bleeding endpoint (percentage of subjects with blood loss reduction <80 ml/cycle and ≥50% reduction in blood loss compared to baseline) and amenorrhea (no bleeding or spotting) for the study described in Example 1.

FIG. A-1: Depicts mean change from baseline in mean dysmenorrhea pain scores in Study EM-I and maintenance of response in its extension study EM-III over 12 Months.

FIG. A-2: Depicts mean change from baseline in mean NMPP Scores in study EM-I and maintenance of response in its extension Study EM-III over 12 months.

FIG. A-3: Depicts mean change from baseline in mean dyspareunia pain scores in Study EM-I and maintenance of response in its extension Study EM-III over 12 Months FIG. A-4: Depicts lumbar spine BMD Z-score box plots at baseline, Month 6 and Month 12 for ELAGOLIX 150 mg QD and 200 mg BID.

FIG. A-5: Depicts rescue opioid pill counts results as mean percentage change from baseline. Significance vs. placebo is indicated for P<0.05 (*) and P<0.001 (***) from an ANCOVA model. Month=35-day interval.

FIG. A-6: Depicts that the baseline Promis Fatigue SF-6a T-Scores, on average, were more than 1 SD above the population norm [mean=50; SD=10].  denotes P<0.01;  shows statistical significance for elagolix arms versus placebo from ANOVA model for fatigue, including treatment as the main factor. The Maximum SF-6a T-Score=76.8.

FIG. A-7: Depicts that Elagolix reduced Fatigue Score from baseline among Endometriosis Patients. Statistical significance versus placebo, P<0.05, <0.01, <0.001 (*,, *), from ANCOVA model for fatigue is shown, including treatment as the main factor and baseline fatigue as a covariate, which compared each treatment group to placebo.

DETAILED DESCRIPTION OF THE INVENTION

Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence.

The term "Elagolix" refers to 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof. Elagolix is an orally active, non-peptide GnRH antagonist and is unlike other GnRH agonists and injectable (peptide) GnRH antagonists. Elagolix produces a dose dependent suppression of pituitary and ovarian hormones in women. Methods of making Elagolix and a pharmaceutically acceptable salt thereof are described in WO 2005/007165, the contents of which are herein incorporated by reference.

Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid may generally be utilized as the free acid or free base. Alternatively, Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid is intended to encompass any and all acceptable salt forms. In a preferred embodiment, Elagolix is present as a sodium salt, Elagolix sodium.

In addition, Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or salts thereof may also form solvates with water or other organic solvents. Such solvates are similarly included within the scope of this invention.

The terms "treat", "treating" and "treatment" refer to a method of alleviating or abrogating a disease and/or its attendant symptoms.

By "pharmaceutically acceptable" it is meant the carrier, diluent or excipient must be compatible with the other ingredients of the formulation and not deleterious to the recipient thereof.

"Solvate" of a compound refers to a molecular complex of the solute (the compound) and the solvent.

The "subject" is defined herein to include animals such as mammals, including, but not limited to, primates (e.g., humans) and the like. In preferred embodiments and aspects, the subject is a human female. In yet another embodiment or aspect, the subject is a premenopausal human female.

"Effective amount" or a "pharmaceutically-effective amount" in reference to Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, or salts thereof, or estrogens or progestogens refers to the amount sufficient to induce a desired biological, pharmacological, or therapeutic outcome in a subject.

The invention generally provides a method of treating endometriosis associated pain wherein the method further reduces fatigue in patients with moderate to severe endometriosis, or wherein the method further reduces use of pain medications in patients with moderate to severe endometriosis. In this method the treatment comprises administering 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof. In one embodiment, Compound A or its pharmaceutically acceptable salt is administered in combination with estrogens and progestogens. The estrogen is selected from the group consisting of estradiol, ethinyl estradiol, and conjugated estrogens. The progestogen is selected from the group consisting of progesterone, norethindrone acetate, norgestimate, drospirenone, and medroxyprogesterone. Preferably, the estrogen is estradiol and the progestogen is norethindrone acetate.

In one embodiment, the estradiol is administered in an amount of about 0.5 mg and the norethindrone acetate is administered in an amount of about 0.1 mg per day. In this embodiment, the estradiol and norethindrone acetate are administered once per day.

In yet another embodiment, the estradiol is administered in an amount of about 1.0 mg and the norethindrone acetate is administered in an amount of about 0.5 mg per day. In this embodiment, the estradiol and norethindrone acetate are administered once per day.

In one aspect of the invention, the estradiol is administered continuously and norethindrone acetate are administered once per day during the last 12-14 days of a menstrual cycle.

In yet another embodiment, the Compound A is dosed 150 mg once-a-day, 200 mg twice-a-day, 300 mg twice-a-day or 600 mg once-a-day.

Therefore, in one embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 300 mg per day. In another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 150 mg per day. 300 mg of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof may be dosed twice a day. 150 mg of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof may also be dosed twice-a-day.

In another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 400 mg per day. In yet another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 200 mg per day.

400 mg of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof may also be dosed twice-a-day. 200 mg of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof may also be dosed twice-a-day.

In yet another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 600 mg per day. Further, in another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In another aspect of the invention, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 28 days. In yet another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 56 days. In another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 84 days. And, in yet another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 168 days. Further, in another embodiment, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for about 168 days to about 1 year.

Preferably, in different aspects of the invention, the estrogen is estradiol and the progestogen is progesterone. In another embodiment, the estradiol is administered continuously and the progesterone is administered once per day during the last 12-14 days of a menstrual cycle.

The invention further provides in one embodiment, a method of reducing fatigue or pain medications in a patient wherein the patient is diagnosed with a condition selected from a group consisting of Uterine Fibroids, Endometriosis, Adenomyosis or Polycystic Ovary Syndrome, the method comprising administering to 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof, wherein fatigue is reduced in said patient or wherein pain medications is reduced to said patient. In one aspect of the patient is diagnosed with a condition selected from a group consisting of Uterine Fibroids, Endometriosis, Adenomyosis or Polycystic Ovary Syndrome. In one embodiment, the patient is diagnosed with Uterine Fibroids. In another embodiment the patient is diagnosed with Endometriosis. In one embodiment the patient is diagnosed with Adenomyosis. In one embodiment the patient is diagnosed with Polycystic Ovary Syndrome.

Methods of Reducing or Managing Heavy Menstrual Bleeding Associated with Uterine Fibroids In one embodiment, the present invention relates to methods for reducing or managing heavy menstrual bleeding (HMB) associated with uterine fibroids in subjects in need of treatment thereof. Heavy menstrual bleeding refers to a subject experiencing greater than 80 mL of blood loss per menstrual cycle (a menstrual cycle is typically 28 days). In contrast, women who do not suffer from heavy menstrual bleeding experience about 30-40 mL of blood loss per menstrual cycle. In one aspect, the methods of the present invention can be used to reduce or manage heavy menstrual bleeding in a subject with uterine fibroids to an amount less than 80 mL of blood loss per cycle. In another aspect, the methods of the present invention can be used to reduce the volume of heavy menstrual bleeding in the subject with uterine fibroids by at least 50% from baseline.

Methods for analyzing menstrual blood loss are known in the art and include, for example, the alkaline hematin method. The alkaline hematin method is based on the quantitation of menstrual blood collected on sanitary products (Hallberg L., Nilsoon L., Determination of Menstrual Blood Loss. *Scand. J. Clin. Lab. Invest.*, 1964; 16:244-248). The method uses a strong alkaline solution to chemically convert the heme from bloodstained sanitary products to alkaline hematin, which is measured colorimetrically. When compared to a subject's serum hemoglobin (Hgb), the volume of blood loss in the menstrual products can be determined.

a. Use of Elagolix or a Pharmaceutically Acceptable Salt Thereof

In one aspect, the methods of the present invention involve reducing or managing heavy menstrual bleeding associated with uterine fibroids in a subject in need of treatment thereof. The methods involve administering to a subject suffering from heavy menstrual bleeding associated with uterine fibroids an effective amount of Elagolix or a pharmaceutically acceptable salt thereof. The effective amount or dose of Elagolix or a pharmaceutically acceptable salt thereof that can be administered to a subject is in the range of 300 to 600 mg. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day.

b. Use of Elagolix or a Pharmaceutically Acceptable Salt Thereof in Combination with Hormone Replacement Therapy In another aspect, the methods of the present invention involve reducing or managing heavy menstrual bleeding associated with uterine fibroids in a subject in need of treatment thereof. The methods involve administering to a subject suffering from heavy menstrual bleeding associated with uterine fibroids an effective amount of Elagolix or a pharmaceutically acceptable salt thereof in combination with one or more estrogens and progestogens. The administration of a combination of estrogen and progestogens to subjects is often referred to as "hormone replacement therapy" or "add-back therapy". The "hormone replacement therapy" or "add-back therapy" is used to prevent hypoestrogenic symptoms such as bone mineral density loss and vasomotor symptoms. Specifically, it was found that when subjects were treated with an effective amount of Elagolix or a pharmaceutically acceptable salt thereof in combination with the estrogens and progestogens, substantially lower number of subjects reported hot flashes (which are a vasomotor symptom of estrogen deprivation) compared to those treated with Elagolix alone.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined oral formulations, used continuously, containing estrogens and progestogens for hormone replacement therapy are known in the art and can also be used in the invention. Suitable formulations include, for example, Activella®, Angeliq®, FemHRT®, Jenteli™, Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is oral progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Reducing Fibroid Volume in a Subject with Uterine Fibroids

In another embodiment, the present invention relates to methods for reducing the fibroid volume in a subject with uterine fibroids. In one aspect, the methods of the present invention can be used to reduce the fibroid volume by greater than or equal to at least about 25%. In another aspect, the methods of the present invention can be used to reduce the fibroid volume in a subject with uterine fibroids. More specifically, the methods of the present invention can be used to reduce the fibroid volume in a subject with uterine fibroids by volume by greater than or equal to at least about 25%. In another aspect, the methods of the present invention are used to reduce the fibroid volume in a subject with uterine fibroids prior to hysterectomy, myomectomy, or uterine artery embolization. Methods for measuring fibroid volume are known in the art and include ultrasound and/or MRI.

a. Use of Elagolix or a Pharmaceutically Acceptable Salt Thereof

In one aspect, the methods of the present invention involve reducing the fibroid volume in a subject with uterine fibroids and in need of treatment thereof. The methods involve administering to a subject suffering with uterine fibroids an effective amount of Elagolix or a pharmaceutically acceptable salt thereof. The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day.

b. Use of Elagolix or a Pharmaceutically Acceptable Salt Thereof in Combination with Hormone Replacement Therapy In another aspect, the methods of the present invention involve reducing the total fibroid volume in a subject with uterine fibroids and in need of treatment thereof. The methods involve administering to a subject suffering with uterine fibroids an effective amount of Elagolix or a pharmaceutically acceptable salt thereof in combination with one or more estrogens and progestogens. The methods involve administering to a subject suffering from heavy menstrual bleeding associated with uterine fibroids an effective amount of Elagolix or a pharmaceutically acceptable salt thereof in combination with estrogens and progestogens.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined formulations, used continuously, containing estogens and progestogens for hormone replacement therapy are known in the art and can also be used in the invention. Suitable formulations include, for example, Activella®, Angeliq®, FemHRT®, Jenteli™ Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Reducing Total Uterine Volume in a Subject with Uterine Fibroids

In another embodiment, the present invention relates to methods for reducing the total uterine volume in a subject with uterine fibroids. The "total uterine volume" is the volume of the entire uterus. In one aspect, the methods of the present invention can be used to reduce the total uterine volume by greater than or equal to at least about 25%. In another aspect, the methods of the present invention can be used to reduce the total uterine volume in a subject with uterine fibroids. More specifically, the methods of the present invention can be used to reduce the total uterine volume in a subject with uterine fibroids by greater than or equal to at least about 25%. Methods for measuring total uterine volume are known in the art and include, ultrasound and/or MRI.

a. Use of Elagolix or a Pharmaceutically Acceptable Salt Thereof

In one aspect, the methods of the present invention involve reducing the total uterine volume in a subject with uterine fibroids and in need of treatment thereof. The methods involve administering to a subject suffering with uterine fibroids an effective amount of Elagolix or a pharmaceutically acceptable salt thereof. The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day.

b. Use of Elagolix or a Pharmaceutically Acceptable Salt Thereof in Combination with Hormone Replacement Therapy In another aspect, the methods of the present invention involve reducing the uterine volume in a subject with uterine fibroids and in need of treatment thereof. The methods involve administering to a subject suffering with uterine fibroids an effective amount of Elagolix or a pharmaceutically acceptable salt thereof in combination with one or more estrogens and progestogens. The methods involve administering to a subject suffering from heavy menstrual bleeding associated with uterine fibroids an effective amount of Elagolix or a pharmaceutically acceptable salt thereof in combination with one or more estrogens and progestogens.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined formulations, used continuously, containing estogens and progestogens for hormone replacement therapy are known in the art and can also be used in the invention. Suitable formulations include, for example, Activella®, Angeliq®, FemHRT®, Jenteli™ Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Preventing Uterine Fibroid Regrowth or Recurrence after Surgical or Semi-Invasive Intervention In still yet another embodiment, the present invention relates to methods for preventing the regrowth or recurrence of uterine fibroids in a subject after removal of one or more uterine fibroids from the subject by surgical (such as myomectomy) or semi-invasive intervention (such as uterine artery embolization, MRI-guided high-intensity focused ultrasound, etc).

a. Use of Elagolix or a Pharmaceutically Acceptable Salt Thereof

In one of the methods of the present invention involve preventing the regrowth or return of uterine fibroids in a subject after removal of one or more uterine fibroids from the subject by surgical or semi-invasive intervention. The methods involve administering to a subject who has had one or more uterine fibroids removed (such as by surgical or semi-invasive intervention) an effective amount of Elagolix or a pharmaceutically acceptable salt thereof.

The Elagolix or pharmaceutically acceptable salt thereof can be administered to a subject in need thereof immediately after surgery. "Immediately after surgery" refers to administration of the Elagolix or pharmaceutically acceptable salt thereof 1 day post surgery, 2 days post surgery, 3 days post surgery, 4 days post surgery, 5 days post surgery, 6 days post surgery or 7 days post surgery. The Elagolix or pharmaceutically acceptable salt thereof can be administered to a subject daily (namely, continuously), post-surgery for a duration of at least 6 months, at least 12 months, at least 18 months, at least 24 months, etc. The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day.

b. Use of Elagolix or a Pharmaceutically Acceptable Salt Thereof in Combination with Hormone Replacement Therapy In still yet another aspect, the methods of the present invention involve preventing the regrowth or recurrence of uterine fibroids in a subject after removal of one or more uterine fibroids from the subject by surgical or semi-invasive intervention. The methods involve administering to a subject who has had one or more uterine fibroids removed (such as by surgical or semi-invasive intervention) an effective amount of Elagolix or a pharmaceutically acceptable salt thereof in combination with one or more estrogens and progestogens.

The Elagolix or pharmaceutically acceptable salt thereof in combination with one or more estrogens and progestogens can be administered to a subject in need thereof immediately after surgery. "Immediately after surgery" refers to administration of the Elagolix or pharmaceutically acceptable salt thereof 1 day post surgery, 2 days post surgery, 3 days post surgery, 4 days post surgery, 5 days post surgery, 6 days post surgery or 7 days post surgery. The Elagolix or pharmaceutically acceptable salt thereof can be administered to a subject daily (namely, continuously), post-surgery for a duration of at least 6 months, at least 12 months, at least 18 months, at least 24 months, etc.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined formulations, used continuously, containing estogens and progestogens for hormone replacement therapy are known in the art and can also be used in the invention. Suitable formulations include, for example, Activella®, Angeliq®, FemHRT®, Jenteli™ Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Reducing or Managing Heavy Menstrual Bleeding not Associated with Uterine Fibroids In one embodiment, the present invention relates to methods for reducing or managing heavy menstrual bleeding (HMB) in subjects in need of treatment thereof where the heavy menstrual bleeding is not associated with uterine fibroids but is the result of other conditions, such as adenomyosis, polycystic ovary syndrome, hereditary bleeding disorders, idiopathic heavy menstrual bleeding, etc. In one aspect, the methods of the present invention can be used to reduce or manage heavy menstrual bleeding to less than 80 mL of blood loss per cycle. In another aspect, the methods of the present invention can be used to reduce the volume of heavy menstrual bleeding in the subject by 50% from baseline.

a. Use of Elagolix or a Pharmaceutically Acceptable Salt Thereof

In one aspect, the methods of the present invention involve reducing or managing heavy menstrual bleeding associated with conditions other than uterine fibroids in a subject in need of treatment thereof. The methods involve administering to a subject suffering from heavy menstrual bleeding associated with conditions other than uterine fibroids an effective amount of Elagolix or a pharmaceutically acceptable salt thereof. In one aspect, the subject may not have any uterine fibroids. In another aspect, the subject may have uterine fibroids but the heavy menstrual bleeding is not a result of the uterine fibroids.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day. The estrogen and/or progestogens can be administered orally, transdermally or intravaginally.

b. Use of Elagolix or a Pharmaceutically Acceptable Salt Thereof in Combination with Hormone Replacement Therapy In another aspect, the methods of the present invention involve reducing or managing heavy menstrual bleeding associated with conditions other than uterine fibroids in a subject in need of treatment thereof. The methods involve administering to a subject suffering from heavy menstrual bleeding associated with conditions other than uterine fibroids an effective amount of Elagolix or a pharmaceutically acceptable salt thereof in combination with one or more estrogens and progestogens. The methods involve administering to a subject suffering from heavy menstrual bleeding associated with uterine fibroids an effective amount of Elagolix or a pharmaceutically acceptable salt thereof in combination with estrogens and progestogens. In one aspect, the subject may not have any uterine fibroids. In another aspect, the subject may have uterine fibroids but the heavy menstrual bleeding is not a result of the uterine fibroids.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined formulations, used continuously, containing estogens and progestogens for hormone replacement therapy are known in the art and can also be used in the invention.

Suitable formulations include, for example, Activella®, Angeliq®, FemHRT®, Jenteli™ Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Treating Uterine Fibroids in Subjects in Need of Treatment Thereof

In one embodiment, the present invention relates to methods for treating subjects having uterine fibroids and in need of treatment thereof. Subjects having uterine fibroids and treated pursuant to this method may not experience heavy menstrual bleeding but instead exhibit other uterine fibroid symptoms such as pelvic pressure, pelvic pain, bloating, urinary symptoms, etc.

a. Use of Elagolix or a Pharmaceutically Acceptable Salt Thereof

In one aspect, the methods of the present invention involve treating subjects having uterine fibroids that do not exhibit heavy menstrual bleeding but are in need of treatment thereof. The methods involve administering to a subject having uterine fibroids (and that does not exhibit heavy menstrual bleeding) an effective amount of Elagolix or a pharmaceutically acceptable salt thereof. The effective amount or dose of Elagolix or a pharmaceutically acceptable salt thereof that can be administered to a subject is in the range 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day. The estrogen and/or progestogens can be administered orally, transdermally or intravaginally.

b. Use of Elagolix or a Pharmaceutically Acceptable Salt Thereof in Combination with Hormone Replacement Therapy In another aspect, the methods of the present invention treating a subject uterine fibroids in a subject in need of treatment thereof. The methods involve administering to a subject having uterine fibroids (and that does not exhibit heavy menstrual bleeding) an effective amount of Elagolix or a pharmaceutically acceptable salt thereof in combination with estrogens and progestogens. The methods involve administering to a subject suffering from uterine fibroids (and that does not exhibit heavy menstrual bleeding) an effective amount of Elagolix or a pharmaceutically acceptable salt thereof in combination with one or more estrogens and progestogens.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined formulations, used continuously, containing estogens and progestogens for hormone replacement therapy are known in the art and can also be used in the invention. Suitable formulations include, for example, Activella®, Angeliq®, FemHRT®, Jenteli™ Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In one embodiment of the invention, the dose of Elagolix, or a pharmaceutically acceptable salt thereof, is in the range of 100 to 800 mg, the range of 200 to 600 mg, the range of 200 to 400 mg, or the range of 300 to 600 mg. In a further embodiment of the invention, the dose of a compound of Elagolix or a pharmaceutically acceptable salt or solvate thereof, is about 75 mg, 100 mg, 150 mg, 200 mg, 300 mg, 400 mg, or 600 mg. The dose can be administered once a day or twice a day.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle comprises daily administration of Elagolix and estrogens and cyclical administration of progestogens.

In still yet a further aspect, the treatment cycle comprises daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Certain embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example-1: Summary of Efficacy and Safety Findings in Completed Phase 2 Studies in Endometriosis Subjects Efficacy Six Phase 2 randomized, double-blind, placebo-, and/or active-controlled, parallel-group, multiple dose studies were completed to evaluate elagolix as a treatment for endometriosis associated pain. Efficacy was assessed for dysmenorrhea (DYS), nonmenstrual pelvic pain (NMPP), dyspareunia, and general pelvic pain with a range of instruments.

Additional efficacy assessments included quality of life and the use of analgesics for control of endometriosis pain.

Across these Phase 2 studies, the enrollment criteria were similar and were intended to select premenopausal women aged 18 to 49 years of age with endometriosis confirmed by visual inspection (laparoscopy or laparotomy within 5 to 8 years of screening) who experienced moderate to severe endometriosis-associated pain. Women were included if they had regular menstrual cycles and no significant uterine fibroids or pelvic lesions.

Total daily doses of elagolix ranging from 75 to 250 mg were evaluated across a range of pain instruments measuring DYS, NMPP, or general pelvic pain (including patient global impression of change), during 12 or 24 weeks of treatment.

Collectively, these Phase 2 studies showed that elagolix daily doses of 100 to 250 mg were associated with clinically meaningful reductions in endometriosis-associated pain.

Studies also demonstrated that an elagolix daily dose of 150 mg had comparable effect to subcutaneous depot medroxyprogesterone acetate (DMPA-SC) on DYS and NMPP, while elagolix daily doses of 150 mg and 250 mg had less effect compared with leuprorelin.

Additionally, symptoms of dyspareunia were reduced and women reported improved quality of life assessments. Overall usage of analgesics for pain control also decreased in the elagolix treatment arms.

The effects of elagolix on uterine bleeding were evaluated in the Phase 2 endometriosis program, with an analysis of the percentage of days of bleeding per month according to daily reporting of bleeding in an electronic diary (eDiary). These analyses showed that overall, patients on elagolix experienced fewer days of bleeding per month compared with patients who received placebo; patients on 250 mg QD experienced fewer days of bleeding compared with patients on 150 mg QD. Review of individual menstrual charts from daily eDiary records showed that the majority of elagolix recipients experienced reduced bleeding intensity and often had extended intervals between bleeding episodes, Some subjects experienced periods of oligomenorrhea with some evidence of irregular bleeding as well, particularly at lower doses of elagolix.

Safety

The safety and tolerability of elagolix in women with endometriosis has been evaluated in 6 completed Phase 2 studies including 708 women who received at least 1 dose of elagolix. Overall, 475 women have received elagolix for at least 12 weeks and 278 women for a period of at least 24 weeks. The majority of women were Caucasian (78.9% to 100%), while approximately 7% were black and approximately 4.5% were Hispanic. The mean age across these six Phase 2 studies was 31 to 33 years (range 18 to 48 years) and mean body mass index (BMI) of 23 to 28 kg/m. Overall, 40% to 70% of women had received prior therapy for the treatment of endometriosis, and hormonal contraceptives were the most common class of drug prescribed for the condition. In addition, the majority were receiving analgesic medications (nonsteroidal anti-inflammatory drugs, opioids, and/or other) prior to study enrollment Review of the safety data in the completed Phase 2 studies in women with endometriosis indicates that elagolix was safe and well tolerated for all daily doses (100 to 250 mg) that were evaluated. The incidence of AEs (4.8%) that led to discontinuations was 4.8%, The most common adverse events observed with elagolix in both the 12-week and 24-week analysis sets were headache and nausea with an incidence similar to that observed with DMPA-SC in the 24-week analysis. None of these events were serious and they contributed to less than 1% of study discontinuations.

Example 2

This example is a Phase 2a, multicenter, double-blind, placebo-controlled, randomized trial (N=280) with a 3-month treatment duration evaluating the safety and efficacy of Elagolix administered with or without Activella® in premenopausal women with uterine fibroids.

It evaluates the safety and efficacy of 6 doses of Elagolix (100 mg BID, 200 mg BID, 200 mg BID plus low dose Activella® (a combination of 0.5 mg estradiol and 0.1 mg northindrone acetate), 300 mg BID, 300 mg BID plus 1.0 mg of Estrace and 200 mg cyclical Prometrium (collectively referred to as "EP"), 400 mg QD and 600 QD) versus placebo (PBO) to reduce uterine bleeding associated with uterine fibroids and to reduce fibroid volume and uterine volume in premenopausal women 20 to 49 years of age with heavy menstrual bleeding (HMB; >80 mL blood loss per menstrual cycle). The study involved the following six (6) cohorts:

Cohort 1: Elagolix 200 mg BID or placebo (PBO).
Cohort 2: Elagolix 300 mg BID or placebo.
Cohort 3: Elagolix 200 mg BID plus low dose Activella® (a combination of 0.5 mg estradiol and 0.1 mg norethindrone actate).
Cohort 4: Elagolix 100 mg BID, 400 mg QD or placebo.
Cohort 5: Elagolix 600 mg QD.
Cohort 6: Elagolix 300 mg BID plus estrogen (1.0 mg of estradiol (Estrace®)) and 200 mg progesterone (cyclical Prometrium®)) (EP). Estrace® was given daily with Elagolix (continuously) and Prometrium® was given daily for the last 12 days of each 28 day menstrual cycle (cyclical).

Enrollment

Preliminary data includes 170 women received at least 1 dose of Elagolix. Overall, 152 women have received Elagolix for at least 2 months and 127 women received Elagolix for 3 months (full treatment duration). The majority of women are black (~80%), with 19% Caucasian. The mean age is 41.9 years (range 28 to 53), and mean body mass index (BMI) is 30.3 kg/m$^2$.

The enrollment characteristics are shown in Table 1 fibroid and uterine volume, respectively. Quality of life (QoL) measures were also determined using the "Responsiveness of the uterine fibroid symptom and health-related quality of life questionnaire" (UFS-QOL) (Harding, Gale, Coyne Karin S., Thompson Christine L., Spies James B, United BioSource Corporation, 7101 Wisconsin Avenue,

TABLE 1

| | Number of patients | | | | | | | | |
|---|---|---|---|---|---|---|---|---|---|
| Dose (Cohort) | E300 BID (2) | E600 QD (5) | E300 BD + EP (6) | E200 BID (1) | E400 QD (4) | E200 BID + A (3) | E100 BID (4) | PBO* (1, 2, 4) | Total |
| Randomized | 30 | 30 | 27 | 35 | 32 | 34 | 33 | 50 | 271 |
| Treated | 30 | 30 | 27 | 35 | 32 | 34 | 33 | 50 | 271 |
| Completed | 26 | 24 | 25 | 28 | 26 | 29 | 26 | 43 | 227 |
| Discontinued | 4 | 6 | 2 | 7 | 6 | 5 | 7 | 7 | 44 |
| Interim Analysis Set | 30 | 30 | 27 | 35 | 32 | 34 | 33 | 50 | 271 |

Baseline characteristics are shown in Table 2.

TABLE 2

| | Number of patients | | | | | | | | |
|---|---|---|---|---|---|---|---|---|---|
| Characteristic | E 300 BID n = 30 | E 600 QD n = 30 | E 300 BID + EP N = 27 | E 200 BID n = 35 | E 400 QD n = 32 | E 200 BID + A n = 34 | E 100 BID n = 33 | PBO n = 50 | Total N = 271 |
| Mean Age (yrs.)* | 42.6 | 40.8 | 41.6 | 43.1 | 40.8 | 40.9 | 42.1 | 42.3 | 41.8 |
| Race White/Black (%) | 20/76.7 | 16.7/80 | 40.7/55.6 | 20.0/80.0 | 15.6/78.1 | 20.6/76.5 | 30.3/69.7 | 24.0/72.0* | 23.2/73.8 |
| Mean Weight (Kg) | 80.7 | 82.5 | 79.4 | 79.6 | 86.0 | 85.7 | 82.8 | 82.1 | 82.4 |
| Mean BMI (kg/m$^2$) | 29 | 31.1 | 29.6 | 29.4 | 31.7 | 31.8 | 30.4 | 29.9 | 30.3 |
| Menstrual Blood Loss (mL)—Mean (Median) | 208 (186) | 216 (179.7) | 265.8 | 333 (193) | 210 (192) | 245 (177) | 261 (210) | 336 (190) | 237 (163) |
| Hemoglobin (g/dL)— Mean | 11.2 | 10.8 | 10.3 | 10.8 | 11.0 | 10.8 | 10.2 | 10.4 | 10.7 |
| Primary Fibroid Volume (cm$^3$) Mean (Median) | 82.7 (47.8) | 86.7 (39.5) | 148.6 (99.3) | 137.9 (55.9) | 47 (27) | 66 (49) | 61 (27) | 101.1 (33.2) | 90.1 (41.1) |
| Uterine Volume (cm$^3$)— Mean (Median) | 575 (519) | 495.7 (364.4) | 658.9 (616.8) | 685 (460) | 416 (322) | 529 (469) | 473 (297) | 493 (351) | 534 (421) |

Sex: All female
*age range 28-53; 15% are >25-≤ 35; 55% are >35-≤45; and 30% are >45
Note: Asian ethnicity, missing data on race and multi-racial subjects account for remaining % on for race Efficacy There are a number of efficacy endpoints, but a composite endpoint consisting of two bleeding assessments was used to assess one measure of efficacy. It included the percent of subjects who achieved a menstrual blood loss (MBL) volume of <80 mL at the Final Month (last 28 days of treatment), and also achieved a ≥50% reduction in MBL volume from baseline to the Final Month (last 28 days of treatment) as measured by the Alkaline Hematin (AH) method. Eighty-five percent (85%), 97%, and 30% of subjects achieved the composite bleeding assessment endpoint in the 200 mg BID, 300 mg BID, and placebo groups, respectively (P<0.05 for 200 mg BID versus placebo in cohort 1, and 300 mg BID versus placebo in cohort 2). Eighty-two percent (82%) of subjects in the 200 mg BID+ low-dose Activella® (low dose Activella® is a combination of (a combination of 0.5 mg estradiol and 0.1 mg norethindrone acetate) group achieved this composite endpoint. With respect to fibroid and uterine volumes, 63%, 55%, and 29% of subjects achieved a ≥25% reduction in fibroid volume and 50%, 68%, and 9% achieved a ≥25% reduction in uterine volume in the 200 mg BID, 300 mg BID, and placebo groups, respectively. In the 200 mg BID+low dose group, 53% and 42% of subjects achieved a ≥25% reduction in Suite 600, Bethesda, Md., 20814, USA, Health and Quality Life Outcomes, 2008, 6, page 99).

The results are summarized in FIGS. 1-5 as well as Tables 3 and 4 below.

Table 3: Total Menstrual Blood Loss during the Treatment Period Measured by Alkaline Hematin (AH) Method (See, also FIG. 2).

TABLE 3

| Dose | Average Total Blood Loss Measured by AH Method During Treatment (in mL) |
|---|---|
| Elagolix 600 QD (N = 24) | 69.6 |
| Elagolix 300 BID (N = 26) | 4.3 |
| Elagolix 400 QD (N = 26) | 38.4 |
| Elagolix 200 BID (N = 28) | 47.0 |
| Elagolix 200 BID + Act (N = 29) | 119.8 |
| Elagolix 300 BID + EP (N = 25) | 114.5 |
| Elagolix 100 BID (N = 26) | 198.4 |
| Placebo (PBO) (N = 43) | 569.7 |

Table 4: Average Monthly Menstrual Blood Loss (MBL) During the Treatment Period Measured by Alkaline Hematin (AH) Method

TABLE 4

| Dose | Number of subjects (N) | Average Blood Loss Per Cycle Measured by AH Method in Screening (mL) | Average total MBL from days 6-35 post-baseline (mL) | Average Total MBL from Days 36-65 Post-Baseline (mL) | Average Total MBL in Days 66-95 Post-Baseline (mL) |
|---|---|---|---|---|---|
| Elagolix 600 QD (N = 24) | 24 | 228.7 | 27.6 | 35.0 | 14.9 |
| Elagolix 300 BID (N = 26) | 26 | 224.8 | 0 | 0 | 4.3 |
| Elagolix 400 QD (N = 26) | 26 | 220.3 | 14.9 | 12.4 | 21.6 |
| Elagolix 200 BID (N = 28) | 28 | 287.4 | 0 | 5.5 | 41.5 |
| Elagolix 200 BID + Act (N = 29) | 29 | 251.9 | 26.3 | 41.5 | 37.9 |
| Elagolix 300 BID + EP (N = 25) | 25 | 253.9 | 32.7 | 40.2 | 46.2 |
| Elagolix 100 BID (N = 26) | 26 | 276.4 | 33.2 | 100.9 | 65.4 |
| Placebo (PBO) (N = 43) | 43 | 271.2 | 190.5 | 194.6 | 190.3 |

Figure 2:
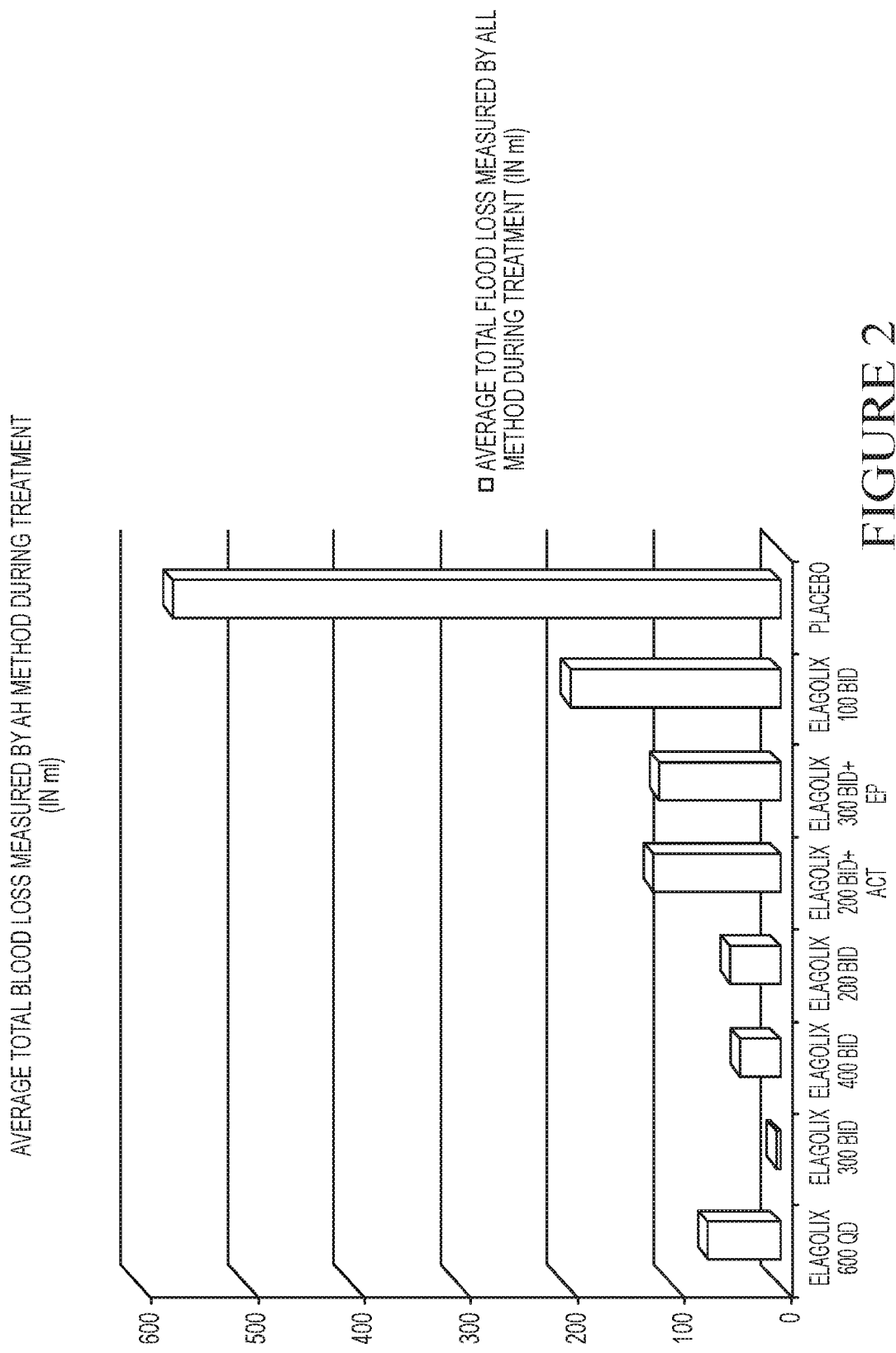
FIG. 2 shows the average total blood loss measured by the alkaline hematin methods during three (3) months of treatment as described in the study in Example 1. Patients were treated with Elagolix 600 QD (N=24), Elagolix 300 BID (N=26), Elagolix 400 QD (N=26), Elagolix 200 BID (N=28), Elagolix 200 BID plus low dose Activella® (a combination of 0.5 mg estradiol and 0.1 mg northindrone acetate), Elagolix 300 BID plus estrogen (1.0 mg of estradiol (Estrace®)) and 200 mg progesterone (cyclical Prometrium®) (collectively referred to as "EP") (N=25); Elagolix 100 BID (N=26) and placebo (PBO) (N=43).
Figure 3:
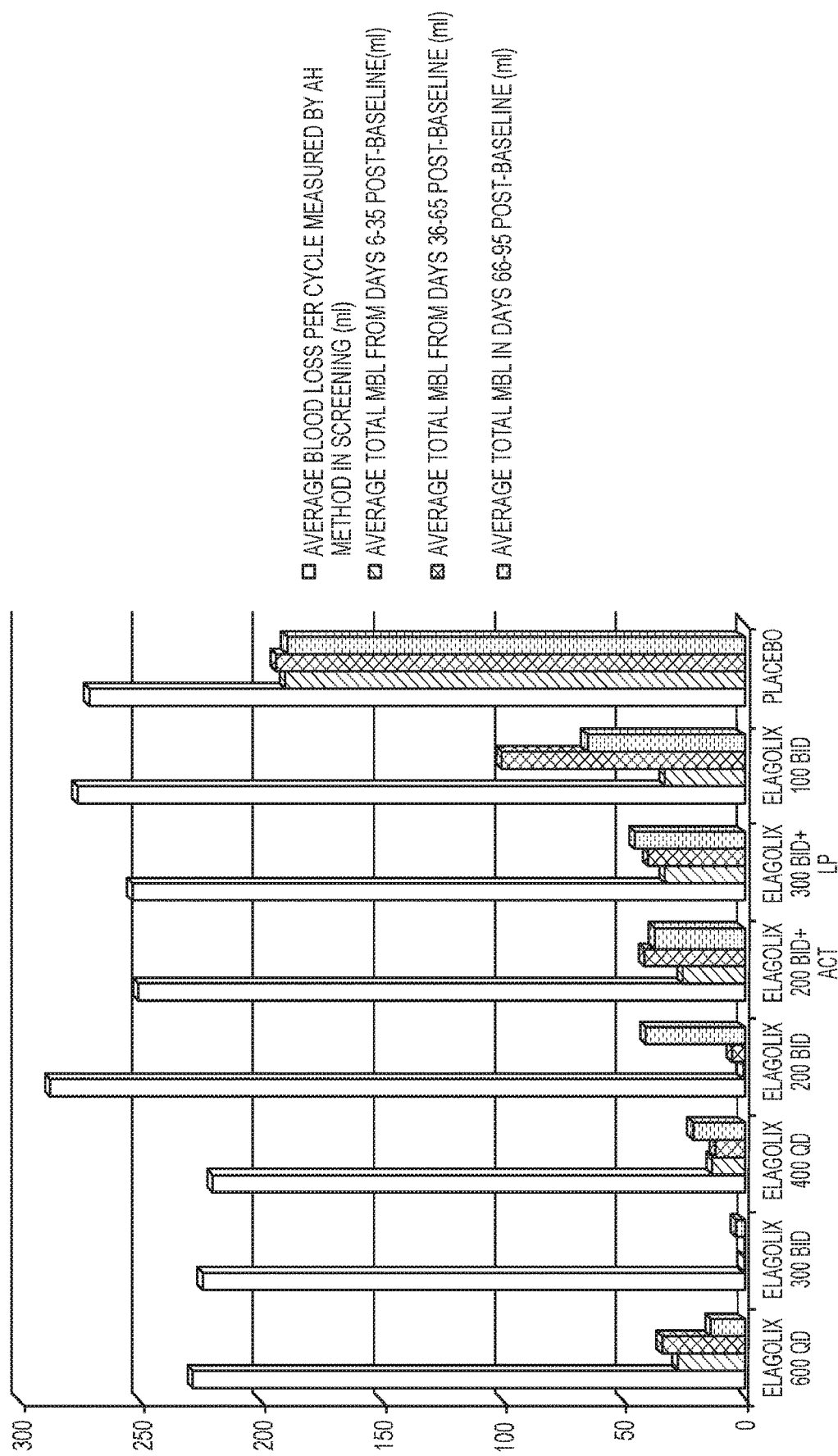
FIG. 3 shows an analysis of the average monthly blood loss (MBL) measured by the alkaline hematin methods during three (3) months of treatment as described in the study in Example 1. Patients were treated with Elagolix 600 QD, Elagolix 300 BID, Elagolix 400 QD, Elagolix 200 BID, Elagolix 200 BID plus low dose Activella® (a combination of 0.5 mg estradiol and 0.1 mg northindrone acetate), Elagolix 300 BID plus estrogen (1.0 mg of estradiol (Estrace®)) and 200 mg progesterone (cyclical Prometrium®); Elagolix 100 BID and placebo. For each of the eight (8) doses shown in FIG. 3, 4 bars are shown. The bar farthest to the left shows the average blood loss per cycle measured by AH method in screening (mL). The second bar is the average total MBL from days 6-35 post-baseline (mL). The third bar is the average total MBL from days 36-65 post-baseline (mL). The fourth bar (furthest to the right) is the average total MBL in days 66-95 post-baseline (mL).

The results in Tables 3 and 4 and FIGS. 1-3 show that Elagolix 300 mg BID without add-back therapy provides the maximum inhibition of bleeding (most of women achieved amenorrhea). Elagolix 400 mg QD and 600 mg QD were slightly less effective in this respect. However, these doses were associated with a relatively high percentage of hot flashes (50-62.5% of women reported an adverse event of hot flash). Elagolix 200 mg plus low-dose Activella® (0.5 mg E2/0.1 mg NETA) and elagolix 300 mg BID plus cyclical EP regimen (1 mg E2/200 mg progesterone for last 12 days of the cycle) restored HMB to normal levels. Both add-back regimens reduced the rate of hot flashes by approximately 50%.

Figure 4:
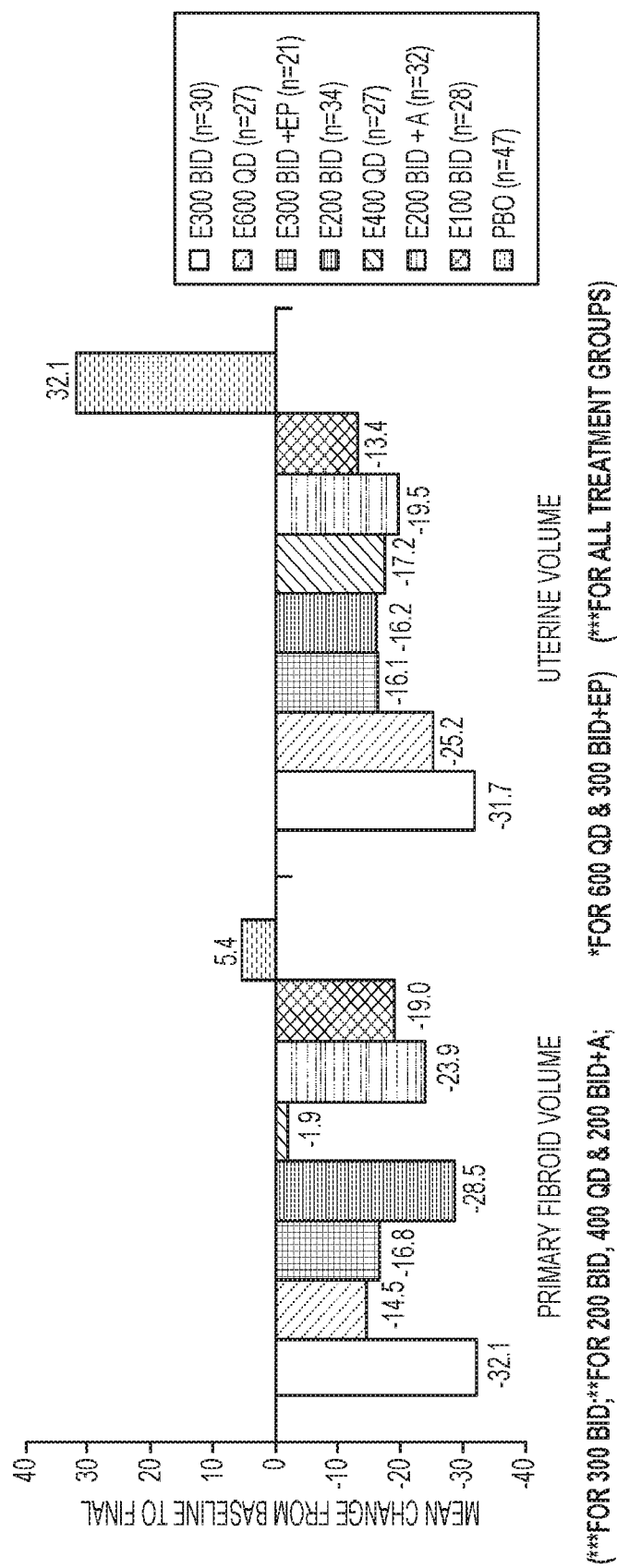
FIG. 4 shows an analysis of the mean percentage (%) change from baseline on each of primary fibroid and uterine volume as described in the study in Example 1. For the primary fibroid volume and uterine volume data shown in FIG. 4, patients were treated with Elagolix 300 BID (N=30) (first bar on the far left), E600 QD (N=27) (second bar from the left), E300+estrogen (1.0 mg of estradiol (Estrace®)) and 200 mg progesterone (cyclical Prometrium®) (referred to as "EP") (N=21) (third bar from the left), E200 BID (N=34) (fourth bar from the left), E400 QD (N=27) (fifth bar from the left), E200 BID+a low dose Activella® (a combination of 0.5 mg estradiol and 0.1 mg northindrone acetate) (referred to as "A") (N=32) (sixth bar from the left), E100 BID (seventh bar from the left) (N=28) and placebo (PBO) (N=47) (eighth bar from the left (or first on the right)). P values are defined as: *p<0.001 for Elagolix vs. pooled placebo (PBO; PBO from cohorts 1, 2 & 4). p<0.01 for Elagolix vs. pooled PBO (PBO from cohorts 1, 2 & 4). *p<0.05 for Elagolix vs. pooled placebo (PBO; PBO from cohorts 1, 2 & 4).
Figure 5:
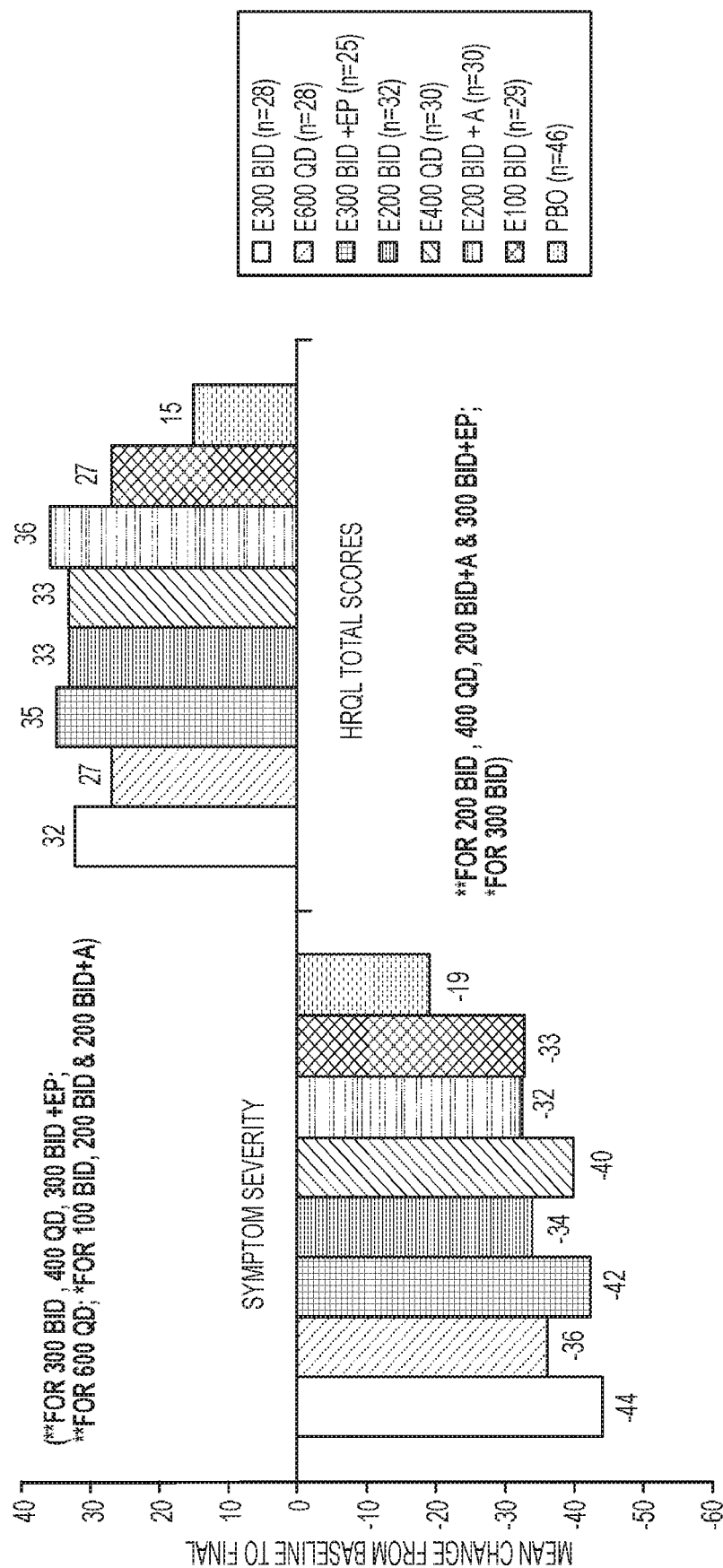
FIG. 5 shows an analysis of uterine fibroid symptom severity and quality of life (UFS-QoL) results as described in the study in Example 1. For the symptom severity and Health Related Quality of Life (HRQL) total scores and uterine volume data shown in FIG. 5, patients were treated with Elagolix 300 BID (N=28) (first bar on the far left), E600 QD (N=28) (second bar from the left), E300+estrogen (1.0 mg of estradiol (Estrace®)) and 200 mg progesterone (cyclical Prometrium®) (referred to as "EP") (N=25) (third bar from the left), E200 BID (N=32) (fourth bar from the left), E400 QD (N=30) (fifth bar from the left), E200 BID+a low dose Activella® (a combination of 0.5 mg estradiol and 0.1 mg northindrone acetate) (referred to as "A") (N=30) (sixth bar from the left), E100 BID (seventh bar from the left) (N=29) and placebo (PBO) (N=46) (eighth bar from the left (or first on the right)). P values are defined as: *p<0.001 for Elagolix vs. pooled placebo (PBO; PBO from cohorts 1, 2 & 4). p<0.01 for Elagolix vs. pooled PBO (PBO from cohorts 1, 2 & 4). *p<0.05 for Elagolix vs. pooled placebo (PBO; PBO from cohorts 1, 2 & 4).

FIG. 4 shows that all Elagolix treatments (with and without add-back therapy) reduced uterine and fibroid volumes within 3 months and Elagolix 300 mg BID showed the strongest effects. Additionally, both add-back therapy regimens did not substantially reduced Elagolix effects on volume reduction. FIG. 5 shows that All Elagolix treatments (with or without add-back therapy) showed an improvement in quality of life (QoL) measures compared to placebo Example A-1: Efficacy and Safety of Elagolix in a Subgroup of Women with Uterine Fibroids and Non-Dominant Adenomyosis Adenomyosis is an estrogen-dependent disease of benign endometrial tissue growth within the uterine muscular tissue, and is associated with heavy menstrual bleeding (HMB) and dysmenorrhea. Adenomyosis occurs when endometrial tissue, which normally lines the uterus, exists within and grows into the muscular wall of the uterus. The displaced endometrial tissue continues to act as it normally would—thickening, breaking down and bleeding—during each menstrual cycle. An enlarged uterus and painful, heavy periods can result. Symptoms most often start late in the childbearing years after having children. The cause of adenomyosis remains unknown, but the disease typically disappears after menopause. For women who experience severe discomfort from adenomyosis, certain treatments can help, but hysterectomy is the only cure. Sometimes, adenomyosis is silent—causing no signs or symptoms—or only mildly uncomfortable. In other cases, adenomyosis may cause: Heavy or prolonged menstrual bleeding, severe cramping or sharp, knifelike pelvic pain during menstruation (dysmenorrhea), menstrual cramps that last throughout your period and worsen as you get older, pain during intercourse and blood clots that pass during your period.

An analysis of the efficacy and safety of elagolix in a subgroup of women with UF and adenomyosis was conducted.

Patients and Methods: A 6-month, randomized, double-blind, placebo-controlled, 2-cohort, phase 2b clinical trial evaluating the safety and efficacy of elagolix (Cohort 1, 300 mg twice daily [BID] and Cohort 2, 600 mg once daily [QD]), elagolix with 0.5 mg estradiol (E2)/0.1 mg norethindrone acetate (NETA), and elagolix with 1.0 mg E2/0.5 mg NETA in premenopausal women with HMB (≥80 mL/month) and UF was conducted. Elagolix studied in this clinical trial comprised the sodium salt of Compound A.

All subjects were evaluated with ultrasound and a subset volunteered to also be evaluated by MRI. Women were excluded from the study if they had evidence of diffuse or segmental adenomyosis as a dominant condition (>50% of the myometrium via ultrasound/MRI). Efficacy and safety were evaluated post hoc in a subgroup of women who had confirmed non-dominant adenomyosis (ultrasound/MRI) at baseline. Menstrual blood loss (MBL) was quantified from sanitary products (alkaline hematin). The composite primary endpoint was the proportion of women who had a ≥50% reduction from baseline in HMB and <80 mL MBL in the last 28 days of treatment. Adverse events (AEs) were recorded.

Results: Of the 567 women treated in the study, 86 women (15%; Cohort 1, n=32; Cohort 2, n=54) had confirmed adenomyosis (ultrasound and/or MRI). The majority (72%) of women with confirmed adenomyosis were Black and 87% had a ≥25 BMI at baseline. The proportion of women in Cohort 1 who had a ≥50% reduction from baseline in HMB and <80 mL menstrual blood loss (MBL) in the last 28 days of treatment were 40% for placebo (n=10), 80% for elagolix 300 mg BID (n=5), 83% for elagolix 300 mg BID with 0.5 mg E2/0.1 mg NETA (n=12), and 100% for elagolix 300 mg BID with 1.0 mg E2/0.5 mg NETA (n=5); and in Cohort 2, 13% for placebo (n=16), 92% for elagolix 600 mg QD (n=13), 93% for elagolix 600 mg QD with 0.5 mg E2/0.1 mg NETA (n=14), and 89% for elagolix 600 mg QD with 1.0 mg E2/0.5 mg NETA (n=9). At least 1 AE, related or unrelated to study drug, was reporting in 90% of the placebo group (n=10) and 77% of elagolix-treated groups (n=22) in Cohort 1 and 88% of the placebo group (n=16) and 67% of the elagolix-treated groups (n=38) in Cohort 2.

Example A-2: Safety and Efficacy of Elagolix in Women with Symptomatic Adenomyosis The safety, efficacy, and tolerability of elagolix 300 mg BID in combination with E2/NETA (estradiol 1 mg/norethindrone acetate 0.5 mg QD), versus Placebo in premenopausal women 18-51 years of age with symptomatic adenomyosis will be assessed in a clinical trial.

Elagolix 300 mg BID equivalent with add-back treatment is expected to reduce heavy menstrual bleeding (HMB) and pelvic pain in women with symptomatic adenomyosis. Other doses of add back and elagolix as previously described may also be used for the treatment of symptomatic adenomyosis.

Various aspects of the evaluation where elagolix may be found to be efficacious and safe may include the following:

a) Reduction in heavy menstrual bleeding to <80 ml/mo with a >50% reduction from baseline in menstrual blood loss (MBL) at Month 6;

b) A clinically meaningful decrease (defined as >30% reduction from baseline) in pelvic pain at Month 3. This assessment will take other co-medications, such as analgesic into consideration as well;

c) Reduction in heavy menstrual bleeding to <80 ml/mo with a >50% reduction from baseline in MBL at Month 3;

d) Reduction in heavy menstrual bleeding to <80 ml/mo with a >50% reduction from baseline in MBL at Month 12;

e) A clinically meaningful decrease (defined as >30% reduction) from baseline in pelvic pain at Month 6. This assessment will take other co-medications, such as analgesic into consideration as well;

f) MBL volume mean change from baseline vs placebo;

g) Suppression of bleeding as defined by amenorrhea+/− spotting;

h) Suppression of menstrual cramps that last throughout the menstrual period;

i) Reduction of pain during intercourse; or j) Reduction of blood clots that pass during menstrual period.

Safety evaluations may include physical examination, vital signs, endometrial assessments (endometrial thickness and biopsy), pelvic ultrasound [TAU (Transabdominal Ultrasound)/TVU (Transvaginal Ultrasound)], clinical laboratory tests and adverse events monitoring.

Example A-3: Safety and Efficacy of Elagolix in Endometriosis Related Conditions (I) ELAGOLIX is an orally administered, short-acting, selective, non-peptide small molecule GnRH receptor antagonist that blocks endogenous GnRH signaling by binding competitively to GnRH receptors in the pituitary gland. Administration of ELAGOLIX results in dose-dependent suppression of luteinizing hormone (LH) and follicle-stimulating hormone (FSH) levels, leading to decreased blood levels of the ovarian sex hormones, estradiol and progesterone. LH and FSH suppression begins within hours of administration and is readily reversible upon discontinuation of ELAGOLIX.

(a) Pharmacodynamics: Effect on Ovulation and Estradiol

During the course of a 3-menstrual cycle study in healthy women, ELAGOLIX 150 mg QD and 200 mg BID resulted in an ovulation rate of approximately 50% and 32%, respectively. In the Phase 3 studies in women with endometriosis, partial suppression of estradiol to approximately 50 pg/mL was observed for ELAGOLIX 150 mg QD, whereas nearly full suppression of estradiol to approximately 12 pg/mL was observed following treatment with ELAGOLIX 200 mg BID.

(b) Effect of ELAGOLIX on QT Interval

ELAGOLIX does not prolong the QTc interval. The effect of elagolix (up to 1200 mg) on QTc interval was evaluated in an active-controlled (moxifloxacin 400 mg) thorough QT study. At 17- to 23-fold (relative to 200 mg BID and 150 mg QD regimens, respectively) of elagolix therapeutic concentrations elagolix did not prolong the QTc interval.

(II) The pharmacokinetic properties of ELAGOLIX in healthy subjects are provided in Table A-1. The steady state pharmacokinetic parameters are presented in Table A-2.

TABLE A-1

Pharmacokinetic Properties of ELAGOLIX in Healthy Subjects

| Absorption | |
| --- | --- |
| Tmax (h) | 1.0 |
| Effect of high-fat meal (relative to fasting) | ↓24% |
| Distribution | |
| % Bound to human plasma proteins | 80 |
| Blood-to-plasma ratio | 0.6 |
| Metabolism | |
| Metabolism | CYP3A (major) Minor pathways include: CYP2D6, CYP2C8, and uridine glucuronosyltransferases (UGTs) |
| Elimination | |
| Major route of elimination | Hepatic metabolism |
| Terminal phase elimination half-life (t½) (h) | 4-6 |
| % of dose excreted in urine | <3 |
| % of dose excreted in feces | 90 |

TABLE A-2

Mean (% CV) Steady State Pharmacokinetic Parameters of ELAGOLIX

| Pharmacokinetic Parameter (Units) | 150 mg QD | 200 mg BID |
| --- | --- | --- |
| Cmax (ng/mL) | 574 (29) | 774 (68) |
| AUCτ (ng · hr/mL) | 1292 (31) | 1725 (57) |

CV: Coefficient of variation
Cmax: peak concentration
AUCτ: area under the plasma concentration-time curve during the dosing interval (τ) i.e., 12 hours for BID, 24 hours for QD.

(III) Pharmacokinetics in Specific Populations (a) Renal Impairment

Elagolix exposures (Cmax and AUC) are not altered by renal impairment. The mean exposures are similar for women with moderate to severe or end stage renal disease (including women on dialysis) compared to women with normal renal function.

(b) Hepatic Impairment

Elagolix exposures (Cmax and AUC) are similar between women with normal hepatic function and women with mild hepatic impairment. Elagolix exposures in women with moderate and severe hepatic impairment are approximately 3-fold and 7-fold, respectively, of exposures from women with normal hepatic function.

(IV) Drug Interaction Studies

Drug interaction studies were performed with ELAGOLIX and other drugs that are likely to be co-administered and with drugs commonly used as probes for pharmacokinetic interactions. Tables A-3 and A-4 summarize the pharmacokinetic effects when elagolix was co-administered with other drugs which showed potentially clinically relevant changes.

TABLE A-3

Drug Interactions: Change in Pharmacokinetic Parameters of Elagolix in the Presence of Co-administered Drug

| Co-administered Drug | Regimen of Co-administered Drug | Regimen of Elagolix | N | Ratio (90% CI)* $C_{max}$ | AUC |
|---|---|---|---|---|---|
| Ketoconazole | 400 mg once daily | 150 mg single dose | 11 | 1.77 (1.48-2.12) | 2.20 (1.98-2.44) |
| Rifampin | 600 mg single dose | 150 mg single dose | 12 | 4.37 (3.62-5.28) | 5.58 (4.88-6.37) |
|  | 600 mg once daily |  |  | 2.00 (1.66-2.41) | 1.65 (1.45-1.89) |

CI: Confidence interval
*ratios for $C_{max}$ and AUC compare co-administration of the medication with elagolix vs. administration of elagolix alone.

TABLE A-4

Drug Interactions: Change in Pharmacokinetic Parameters of Co-administered Drug in the Presence of Elagolix

| Co-administered Drug | Regimen of Co-administered Drug | Regimen of Elagolix | N | Ratio (90% CI)* $C_{max}$ | AUC |
|---|---|---|---|---|---|
| Digoxin | 0.5 mg single dose | 200 ms twice daily × 10 days | 11 | 1.71 (1.53-1.91) | 1.26 (1.17-1.35) |
| Rosuvastatin | 20 mg once daily | 300 mg twice daily × 7 days | 10 | 0.99 (0.73-1.35) | 0.60 (0.50-0.71) |
| Midazolam | 2 mg single dose | 300 mg twice daily × 11 days | 20 | 0.56 (0.51-0.62) | 0.46 (0.41-0.50) |
|  |  | 150 ms once daily × 13 days | 11 | 0.81 (0.74-0.89) | 0.65 (0.58-0.72) |
| Norethindrone | 0.35 mg once daily × 112 days | 150 mg once daily × 56 days | 32 | 0.95 (0.86-1.05) | 0.88 (0.79-0.99) |
| Ethinyl Estradiol | Ethinyl estradiol |  |  | 1.15 (1.07-1.25) | 1.30 (1.19-1.42) |
| Norelgestromin[a] | 35 mcg and triphasic | 150 ms once daily | 21 | 0.87 (0.78-0.97) | 0.85 (0.78-0.92) |
| Norgestrel[a] | norgestimate 0.18/0.215/0.25 mg once daily |  |  | 0.89 (0.78-1.00) | 0.92 (0.84-1.01) |

CI: Confidence interval
*ratios for $C_{max}$ and AUC compare co-administration of the medication with elagolix vs. administration of the medication alone.
[a] metabolite of norgestimate (V) Drug Interactions (a) Potential for ELAGOLIX to Affect Other Drugs Elagolix is a weak to moderate inducer of cytochrome P450 (CYP) 3A enzyme. Co-administration with ELAGOLIX may decrease plasma concentration of drugs that are substrates of CYP3A.

Elagolix is an inhibitor of efflux transporter P-glycoprotein (P-gp) at 200 mg BID or higher, such as 300 mg BID or 400 mg QD or 600 mg QD. Co-administration with ELAGOLIX 200 mg BID may increase plasma concentration of drugs that are substrates of P-gp.

(b) Potential for Other Drugs to Affect ELAGOLIX

Elagolix is a substrate of CYP3A, P-gp, and organic anion transporting polypeptide (OATP)1B1. Clinically meaningful interactions are not expected when ELAGOLIX is co-administered with drugs that inhibit CYP3A or P-gp.

Co-administration of ELAGOLIX with drugs that induce CYP3A may decrease elagolix plasma concentrations.

Co-administration of ELAGOLIX with drugs that inhibit OATP1B1 may increase elagolix plasma concentrations. Use of potent OATP1B1 inhibitors are not recommended with ELAGOLIX 200 mg BID regimen.

(c) Established and Other Potential Drug Interactions

Table A-5 provides the effect of co-administration of ELAGOLIX on concentrations of concomitant drugs and the effect of concomitant drugs on elagolix.

TABLE A-5

Established Drug Interactions Based on Drug Interaction Trials

| | | |
|---|---|---|
| Antiarrhythmics digoxin | ↑ digoxin | Clinical monitoring is recommended for digoxin when co-administered with ORILISSA. |
| Antimycobacterial rifampin | ↑ elagolix | Concomitant use of ORILISSA 200 mg twice daily and rifampin is not recommended. Limit concomitant use of ORILISSA 150 mg once daily and rifampin to 6 months. |
| Benzodiazepines oral midazolam | ↓ midazolam | Consider increasing the dose of midazolam and individualize therapy based on the patient's response. |

TABLE A-5-continued

Established Drug Interactions Based on Drug Interaction Trials

| Statins rosuvastatin | ↓ rosuvastatin | Consider increasing the dose of rosuvastatin. |

See Clinical Pharmacology, Tables A-3 and A-4.
The direction of the arrow indicates the direction of the change in AUC (↑=increase, ↓=decrease).

(d) Drugs with No Observed Clinically Significant Interactions with ELAGOLIX

No dose adjustment is required when ELAGOLIX is co-administered with the following medications: ketoconazole, fluconazole, sertraline, and norethindrone or other progestin-only contraceptives.

(VI) Nonclinical Toxicology (a) Carcinogenesis

The 2-year carcinogenicity studies (conducted in mice and rats) revealed no increase in tumors in mouse at any dose, but an increase in thyroid (male and female) and liver (males only) tumors occurred in rat at the high dose (13-fold margin of safety with respect to 200 mg BID in women). The rat tumors were identified as being species-specific and of negligible relevance to humans. This conclusion is based on a follow-on thyroid and hepatic effects-related investigative study performed to document the possibility that thyroid and liver tumors may be specific to rat and occurred via induction of hepatic drug metabolizing enzymes at the high dose.

(b) Mutagenesis

Mutagenicity studies have been performed with elagolix using in vitro and in vivo test systems. These studies provided no evidence of a mutagenic or clastogenic potential.

(c) Impairment of Fertility

Effects on fertility and reproductive organs were evaluated in studies with rats and monkeys that achieved plasma concentrations less than the AUC at MRHD for rats and approximately 0.28-fold to 9.9-fold in monkeys, when adjusted for species difference in GnRH receptor binding affinity. In rats there was no effect in a fertility study (doses 50, 150, 300 mg/kg/day) but involution and a decrease in corpora lutea in ovaries were observed in a repeat-dose study (doses 600, 800 mg/kg/day). In a monkeys repeat-dose study (75, 150, 300 and 600 mg/kg/day), a reversible atrophy of reproductive organs (cervix, uterus and vagina) was observed at all doses. Based on pharmacologic actions of elagolix in humans a reversible effect on fertility may be expected in women.

(VII) Clinical Studies

The efficacy of ELAGOLIX 150 mg QD and 200 mg BID in the management of endometriosis with associated pain was demonstrated in two international double-blind, placebo-controlled studies in 1686 premenopausal women (Study EM-I and EM-II), and two uncontrolled, blinded extension studies (Study EM-III and EM-IV). Each placebo-controlled study assessed the reduction in endometriosis-associated pain over 6 months of treatment. More than 75 percent of women who completed Study EM-I and EM-II enrolled in the extension studies for an additional 6 month treatment period. Subjects were followed for up to 12 months post-treatment.

(a) Reduction in Pain

The co-primary efficacy endpoints were the proportion of responders for dysmenorrhea and pelvic pain not related to menses (also known as non-menstrual pelvic pain [NMPP]) at Month 3 compared to placebo. The primary analysis independently evaluated these endpoints using a daily diary that asked patients to assess their pain and its impact on their daily activities, over the previous 24 hours. The Daily Endometriosis Pain Impact Scale, consisted of patient reported pain levels of None, Mild, Moderate or Severe (correlating with score of 0 to 3, respectively) and included a functional component for each score.

Women were defined as responders if they experienced clinically meaningful reduction in dysmenorrhea and/or NMPP with no increased analgesic use for endometriosis associated pain.

A higher proportion of women treated with ELAGOLIX 150 mg QD or 200 mg BID were responders for dysmenorrhea and NMPP versus placebo in a dose-dependent manner at Month 3. The persistence of efficacy was observed through Month 6 [see Table A-6].

Dyspareunia was evaluated as a secondary endpoint using the Daily Endometriosis Pain Impact Scale.

A higher proportion of women treated with ELAGOLIX 200 mg BID reported clinically meaningful reduction in dyspareunia versus placebo at Month 3 through Month 6.

TABLE A-6

Proportion and Number of Responders† for Dysmenorrhea, Non-Menstrual Pelvic Pain and Dyspareunia at Month 3 and Month 6 in Studies EM-I and EM-II, using the Daily Endometriosis Pain Impact Scale

|  | Study EM-I | | | Study EM-II | | |
|  | ELAGOLIX | | | ELAGOLIX | | |
|  | 150 mg QD %/(n/N) | 200 mg BID %/(n/N) | Placebo %/(n/N) | 150 mg QD %/(n/N) | 200 mg BID % (n/N) | Placebo % (n/N) |
|---|---|---|---|---|---|---|
| Dysmenorrhea (Month 3) | 46.4*** (115/248) | 75.8*** (185/244) | 19.6 (73/373) | 43.4%*** (96/221) | 72.4*** (163/225) | 22.7 (80/353) |
| Dysmenorrhea (Month 6)α | 42.1*** (104/247) | 75.3*** (183/243) | 23.1 (86/372) | 46.2%*** (102/221) | 76.9*** (173/225) | 25.4 (90/355) |
| Non-Menstrual Pelvic Pain (Month 3) | 50.4*** (125/248) | 54.5*** (133/244) | 36.5 (136/373) | 49.8*** (110/221) | 57.8*** (130/225) | 36.5 (129/353) |
| Non-Menstrual Pelvic Pain (Month 6)α | 45.7** (113/247) | 62.1*** (151/243) | 34.9 (130/372) | 51.6%** (114/221) | 62.2*** (140/225) | 40.6 (144/355) |

TABLE A-6-continued

Proportion and Number of Responders† for Dysmenorrhea, Non-Menstrual Pelvic Pain and Dyspareunia at Month 3 and Month 6 in Studies EM-I and EM-II, using the Daily Endometriosis Pain Impact Scale

|  | Study EM-I | | | Study EM-II | | |
|---|---|---|---|---|---|---|
|  | ELAGOLIX | | | ELAGOLIX | | |
|  | 150 mg QD %/(n/N) | 200 mg BID %/(n/N) | Placebo %/(n/N) | 150 mg QD %/(n/N) | 200 mg BID % (n/N) | Placebo % (n/N) |
| Dyspareunia α (Month 3) | 39.6 (74/187) | 47.1*** (81/172) | 31.9 (90/282) | 44.0 (70/159) | 53.7** (87/162) | 39.5 (101/256) |
| Dyspareunia α (Month 6) | 39.6 (74/187) | 50.3*** (81/161) | 33.3 (90/270) | 39.9 (65/163) | 55.8*** (92/165) | 39.4 (100/254) |

†A responder had a reduction in pain from baseline to the analysis month greater than or equal to a calculated, clinically important threshold of improvement, and also had stable or decreased rescue analgesic use.
αA secondary endpoint
*, , *P ≤ 0.001, 0.01, and 0.05, respectively, for test of difference from placebo Both ELAGOLIX treatment groups showed mean decreases from Baseline in dysmenorrhea scores that were statistically significantly greater than placebo beginning at Month 1 and persisted through Month 6.

Women in these studies also provided a daily self-assessment of their endometriosis pain using the Numeric Rating Scale (NRS), on a scale ranging from 0 (no pain) to 10 (worst pain ever). Women taking ELAGOLIX 150 mg QD and 200 mg BID reported a highly statistically (p<0.001) significant reduction in NRS scores compared to placebo at Month 3 and Month 6.

In the two blinded extension studies EM-III and EM-IV, where the patients who were originally on ELAGOLIX in the controlled studies EM-I and EM-II were maintained on their dose, the durability of improvement in dysmenorrhea, NMPP and dyspareunia was demonstrated for a total of 12 months. In study EM-IV, efficacy was maintained when ELAGOLIX was taken with and without food.

Results on efficacy endpoints from Study EM-II were consistent with those observed in Study EM-I.

(b) Reduction in Pain Medication Use

In these studies, women taking ELAGOLIX 200 mg BID reduced the amount of opioid (hydrocodone with acetaminophen) or naproxen rescue medication used to treat their endometriosis-associated pain compared to the amount required at baseline. In addition, there was a significant reduction in the percentage of days per month of the opioid or naproxen rescue medication use for women taking ELAGOLIX 200 mg BID compared to women taking placebo. These effects were less consistently observed for women taking ELAGOLIX 150 mg QD. See FIG. A-5. Compared with placebo, the 200 mg BID elagolix group had a significant decrease from baseline in the percent change of averaged daily opioid pills at Months 3 through 6. Reduction in pain may be reflected by reduction in pain medication, such as prescription opioids or non-steroidal anti-inflammatory agents (NSAIDs) that may be prescribed or found over the counter, for example, naproxen or acetaminophen. 150 mg once a day or twice a day is also expected to reduce intake of pain medication and show reduction in pain, similarly 300 mg doses whether taken once a day or twice a day, is also expected to reduce intake of pain medication and show reduction in pain. In this pooled analysis of rescue analgesic use in two phase 3 trials, compared with placebo: (1) both doses of elagolix 150 QD and 200 BID, showed a significant reduction in the percentage of days in which rescue opioid medication was taken; (2) 200 mg BID elagolix dose showed a significant reduction in the mean percent daily pill counts; (3) fewer women in each elagolix group had increases in the opioid dose and more women had a decreased or stable opioid dose.

In EM-1 and EM-2, 59% and 60% of patients used an opioid rescue analgesic for pain at baseline. The opioid rescue analgesics used at baseline were predominantly hydrocodone/acetaminophen (HC/APAP) and codeine/APAP at strengths of 5/300-325 mg and 30/300-500 mg. In EM-1, of all patients on an opioid at baseline, 98% and 2% were on HC/APAP and codeine/APAP, respectively. In EM-2, of all patients on an opioid at baseline, 50% were on HC/APAP, 16% were on codeine/APAP, 3% were on codeine, and 32% were on tramadol/APAP.

(c) Effects on Bleeding Patterns

Effects on Menstrual Bleeding Patterns

The effects of elagolix on menstrual bleeding were evaluated for up to 12 months using an electronic daily diary where subjects classified their flow of menstrual bleeding (if present in the last 24 hours) as spotting, light, medium, or heavy. elagolix led to a dose-dependent reduction in mean number of bleeding and spotting days and bleeding intensity in those subjects who reported menstrual bleeding.

TABLE B-3

Mean Bleeding/Spotting Days and Mean Intensity Scores at Month 3

|  | Elagolix 150 mg Once Daily | | Elagolix 200 mg Twice Daily | | Placebo | |
|---|---|---|---|---|---|---|
|  | Baseline | Month 3 | Baseline | Month 3 | Baseline | Month 3 |
| Mean bleeding/ spotting days in prior 28 days | 5.3 | 2.8 | 5.7 | 0.8 | 5.4 | 4.6 |
| Mean Intensity score$^a$ | 2.6 | 2.2 | 2.5 | 2.0 | 2.6 | 2.4 |

$^a$Intensity for subjects who reported at least 1 day of bleeding or spotting during 28 day interval. Scale ranges from 1 to 4, 1 = spotting, 2 = light, 3 = medium, 4 = heavy Elagolix also demonstrated a dose-dependent increase in the percentage of women with amenorrhea (defined as no bleeding or spotting in a 56-day interval) over the treatment period. The incidence of amenorrhea during the first six months of treatment ranged from 6-17% for elagolix 150 mg once daily, 13-52% for elagolix 200 mg twice daily and less than 1% for placebo. During the second 6 months of treatment, the incidence of amenorrhea ranged from 11-15% for elagolix 150 mg once daily and 46-57% for elagolix 200 mg twice daily.

After 6 months of therapy with elagolix 150 mg once daily, resumption of menses after stopping was reported by 59%, 87%, and 95% of women within 1, 2, and 6 months respectively. After 6 months of therapy with elagolix 200 mg twice daily, resumption of menses after stopping treatment was reported by 60%, 88%, and 97% of women within 1, 2, and 6 months, respectively.

After 12 months of therapy with elagolix 150 mg once daily resumption of menses after stopping treatment was reported by 77%, 95% and 98% of women within 1, 2, and 6 months respectively. After 12 months of therapy with elagolix 200 mg twice daily resumption of menses after stopping treatment was reported by 55%, 91% and 96% of women within 1, 2, and 6 months respectively.

(VII) Lactation

Risk Summary: No human studies have been conducted to assess the impact of ELAGOLIX on milk production, its presence in breast milk, or its effects on the breastfed child. It is not known whether ELAGOLIX and its metabolites are present in human breast milk, affect human milk production or have effects on the breastfed infant.

(a) In Rats Elagolix is Secreted Minimally Via Milk.

The developmental and health benefits of breastfeeding should be considered along with the mother's clinical need for ELAGOLIX and any potential adverse effects on the breastfed child from ELAGOLIX.

(b) Data: Animal Data

Pregnant rats were given diet containing elagolix throughout the gestation and lactation periods to achieve a daily elagolix dose of 400 mg/kg. During nursing the dams and litters were divided into restricted feeding and non-restricted groups to determine whether elagolix was secreted in the mother's milk. At post natal day 10 and 20 elagolix plasma concentrations in pups of the restricted feeding litters were not measurable. In pups of the non-restricted feeding group, elagolix plasma concentrations were measurable and approximately 1% of the mother's plasma concentrations. Using plasma concentrations in pups as a surrogate of exposure via lactation elagolix is considered to be minimally secreted in milk.

(IX) Adverse Reactions (a) Clinical Trials Experience

Because clinical trials are conducted under widely varying conditions, adverse reaction rates observed in the clinical trials of a drug cannot be directly compared to rates in the clinical trials of another drug and may not reflect the rates observed in clinical practice.

The safety of ELAGOLIX was evaluated in two six-month placebo-controlled clinical studies (Study EM-I and Study EM-II) in which a total of 952 women were treated with 150 mg QD or with 200 mg BID. The population age range was 18-49 years old. Women who completed six months of treatment and met eligibility criteria continued treatment in two blinded six-month extension studies, for a total treatment duration of up to 12 months.

(b) Adverse Reactions (>1%) Leading to Study Discontinuation

In the two controlled studies (EM-I and EM-II), 5.5% of patients treated with ELAGOLIX 150 mg QD and 9.6% of patients treated with ELAGOLIX 200 mg BID discontinued therapy due to adverse reactions. Discontinuations for both dosage forms were most commonly due to hot flush (0.8% and 2.5%) and nausea (0.8% and 1.5%). The majority of discontinuation due to hot flushes and nausea occurred within the first 2 months of therapy. No woman discontinued ELAGOLIX 150 mg QD for hot flushes during the extension study after receiving it for 6 months in the controlled study.

(c) Common Adverse Reactions:

Adverse reactions reported in ≥5% of women in the two placebo-controlled studies in either ELAGOLIX dose group and at a greater frequency than placebo are noted in the following table A-7.

TABLE A-7

Percentage of Patients in Studies EM-I and EM-II with Treatment-Emergent Adverse Reactions Occurring in at Least 5% of Patients (either ELAGOLIX Dose Group) and Greater than Placebo

| | ELAGOLIX 150 mg QD N = 475 % | ELAGOLIX 200 mg BID N = 477 % | Placebo N = 734 % |
|---|---|---|---|
| Gastrointestinal Disorders | | | |
| Nausea | 11 | 16 | 13 |
| Infections and Infestations | | | |
| Nasopharyngitis | 6 | 6 | 4 |
| Sinusitis | 5 | 6 | 4 |
| Upper Respiratory Tract Infection | 6 | 4 | 5 |
| Musculoskeletal and Connective Tissue Disorder | | | |
| Arthralgia | 3 | 5 | 3 |
| Nervous System Disorders | | | |
| Headache | 17 | 20 | 12 |
| Psychiatric Disorders | | | |
| Anxiety | 3 | 5 | 3 |
| Insomnia | 6 | 9 | 3 |
| Reproductive System and Breast Disorders | | | |
| Amenorrhoea* | 4 | 7 | <1 |
| Vascular Disorders | | | |
| Hot Flush | 23 | 45 | 9 |

*[See Clinical Studies - Effects on Bleeding Patterns (VII)]

In the extension studies, the adverse reaction profile was similar to that noted in Placebo-controlled studies, as noted in Table A-7.

(d) Less Common Adverse Reactions:

In EM-I and EM-II, adverse reactions reported in ≥3% and <5% in either ELAGOLIX dose group and greater than placebo included:

Investigations: weight increased;

Psychiatric Disorders: depression, irritability, libido decreased, mood swings;

Gastrointestinal Disorders: diarrhoea, abdominal pain, constipation;

Nervous System Disorders: dizziness; or

Skin and Subcutaneous Tissue Disorders: night sweats.

Events of hot flushes were dose-dependent and the majority were assessed as mild to moderate. All other adverse events were comparable between both doses of ELAGOLIX. The addition of low dose hormone add-back therapy may reduce the occurrence of symptoms associated with estrogen reductions such as hot flush.

(e) Changes in Bone Mineral Density

In the placebo-controlled and extension clinical studies, BMD was measured by DXA. The BMD data of the lumbar spine from these studies are presented in Table A-8. Changes observed in BMD at other anatomical sites (femoral neck, total hip) were generally smaller than lumbar spine.

TABLE A-8

Mean Percentage Change From Baseline in Bone Mineral Density and Percent of Subjects with Z-score ≤−1.5 of Lumbar Spine

| | ELAGOLIX 150 mg QD | | | ELAGOLIX 200 mg BID | | |
|---|---|---|---|---|---|---|
| | N | Mean Percent Change (95% CI) | % Subjects Z-score ≤−1.5 | N | Mean Percent Change (95% CI) | % Subjects Z-score ≤−1.5 |
| On Treatment | | | | | | |
| Month 6 | 360 | −0.52 (−0.79, −0.26) | 0.8% | 365 | −2.54 (−2.81, −2.28) | 4.1% |
| Month 12 | 235 | −0.87 (−1.29, −0.45) | 1.3% | 217 | −3.76 (−4.19, −3.32) | 5.1% |

Following 12 months of ELAGOLIX treatment, no patient on the 150 mg daily dose and less than 1% of patients on the 200 mg BID dose had a Z-score below the normal lower bound of −2.0. In both ELAGOLIX treatment groups, there was progressive recovery of BMD at three DXA sites: lumbar spine, total hip and femoral neck at post-treatment months 6 and 12.

Additional analysis from exposure-response modeling shows that for ELAGOLIX 150 mg QD, the predicted mean (95% CI) Z-score is 0.23 (0.01-0.45) and 0.18 (−0.04-0.40) at Months 12 and 24, respectively. The model predicts that in subjects who initiate treatment on ELAGOLIX 150 mg QD for 3 months then increase the dose to 200 mg BID, the predicted mean (95% CI) Z-score is 0.23 (−0.01-0.47) and 0.11 (−0.13-0.36) at Months 6 and 12, respectively.

(f) Changes in Laboratory Values During Treatment
(i) Lipids

While dose-dependent increases in total cholesterol, low-density lipoprotein cholesterol (LDL-C), high density lipoprotein cholesterol (HDL-C), and triglycerides were noted during ELAGOLIX treatment, these values remained generally within the normal range.

Lipid increases typically occurred within 1 to 2 months after the start of ELAGOLIX therapy and remained stable thereafter over 12 months. Elevated levels of lipids returned to baseline one month after stopping treatment.

The mean increase from pretreatment baseline in LDL-C was 5.25 mg/dL for 150 mg QD and 13.10 mg/dL for 200 mg BID. The mean increase from pretreatment baseline in HDL-C was 2.24 mg/dL for 150 mg QD and 4.16 mg/dL for 200 mg BID. The mean increase from pretreatment baseline in triglycerides was 0.42 mg/dL for 150 mg QD and 11.08 mg/dL for 200 mg BID following 6-month treatment of ELAGOLIX.

Changes in lipid ratios were minimal due to increases in both LDL-C and HDL-C.

Lipid profiles should be assessed and managed according to current clinical practice guidelines.

(ii) Endometrial Safety

Endometrial biopsies were performed in subjects in Study EM-I and its extension at Month 6 and Month 12. The results indicate a dose-dependent decrease in proliferative and secretory biopsy patterns and an increase in quiescent/minimally stimulated biopsy patterns. There were no abnormal biopsy findings post-baseline, such as endometrial hyperplasia or cancer.

Based on transvaginal ultrasound, during the course of a 3-menstrual cycle study in healthy women, ELAGOLIX 150 mg QD and 200 mg BID resulted in a dose dependent decrease in the mean endometrial thickness compared to the pretreatment values.

(X) Decrease in Bone Mineral Density

ELAGOLIX reduces serum estradiol levels in a dose-dependent manner that may also be associated with a dose-dependent decrease in bone mineral density (BMD). There is progressive recovery of BMD at 6 and 12 months after stopping treatment [see Adverse Reactions (6.1)].

Assess BMD by dual-energy x-ray absorptiometry (DXA) after 12 months of continuous use. Discontinue ELAGOLIX if BMD Z-score is lower than −2.0 until BMD is in the age-appropriate range.

If use of ELAGOLIX continues for longer than 12 months, it is recommended that BMD be assessed as clinically indicated. The loss of BMD in premenopausal women should be considered in the benefit/risk assessment for women receiving ELAGOLIX for continuous long-term use.

Consider assessment of BMD sooner than annually in patients at greater risk of low BMD. Risk factors include: taking ELAGOLIX 200 mg twice daily, a Z-score of less than −2.0 after a previous course of treatment with ELAGOLIX, prior use of GnRH agonists, metabolic bone disease, chronic alcohol and/or tobacco use, anorexia nervosa, strong family history of osteoporosis, or chronic use of drugs that can reduce bone mass such as anticonvulsants or corticosteroids.

Although there are no studies addressing whether calcium and vitamin D may lessen BMD loss in women using ELAGOLIX, all patients should have adequate calcium and vitamin D intake.

Clinical studies with GnRH analogs or ELAGOLIX (in other populations) suggest the use of low dose hormonal add-back therapy (estrogens/progestins or norethindrone acetate) may be effective in reducing the bone mineral loss which occurs with these agents alone.

(XI) Dosage and Administration
(a) Dosing Information

ELAGOLIX will be available as either 150 mg tablets (once daily, QD) or 200 mg tablets (twice daily, BID), 150 mg BID, 300 mg BID or 400 mg QD or 600 mg QD to be taken orally with or without food.

(b) Dosing Recommendation

Based on the severity of symptoms and treatment objectives, use the lowest effective dose [see Clinical Studies (VII)]. Treatment with ELAGOLIX may be initiated at any time during a patient's menstrual cycle.

TABLE B-1

In one embodiment, the recommended Dosage and Duration of Use

| Dosing Regimen | Maximum Treatment Duration | Coexisting Condition |
|---|---|---|
| Initiate treatment with ORILISSA 150 mg once daily | 24 months | None |
| Consider initiating treatment with ORILISSA 200 mg twice daily | 6 months | Dyspareunia |
| Initiate treatment with ORILISSA 150 mg once daily. Use of 200 mg twice daily is not recommended. | 6 months | Moderate hepatic impairment (Child-Pugh Class B) |

No dosage adjustment of elagolix is required in women with mild hepatic impairment (Child-Pugh A).

Compared to women with normal liver function, those with moderate hepatic impairment had approximately 3-fold higher elagolix exposures and those with severe hepatic impairment had approximately 7-fold higher elagolix exposures. Because of these increased exposures and risk for bone loss: Elagolix 150 mg once daily is recommended for women with moderate hepatic impairment (Child-Pugh B) with the duration of treatment limited to 6 months. Use of elagolix 200 mg twice daily is not recommended for women with moderate hepatic impairment. Elagolix is contraindicated in women with severe hepatic impairment (Child-Pugh C).

Each tablet contains 155.2 mg of elagolix sodium equivalent to 150 mg of elagolix. Each tablet contains 207.0 mg of elagolix sodium equivalent to 200 mg of elagolix.

(c) Renal Impairment

No dose adjustment of ELAGOLIX is required in women with any degree of renal impairment or end-stage renal disease (including women on dialysis) [see Use in Specific Populations and Clinical Pharmacology].

(d) Hepatic Impairment

No dosage adjustment of ELAGOLIX is required in women with mild hepatic impairment (Child-Pugh A). ELAGOLIX 150 mg QD regimen is recommended in women with moderate hepatic impairment (Child-Pugh B); the 200 mg BID regimen is not recommended.

ELAGOLIX is contraindicated in women with severe hepatic impairment (Child-Pugh C).

Hepatic Transaminase Elevations

In clinical trials, dose-dependent elevations of serum alanine aminotransferase (ALT) at least 3-times the upper limit of the reference range occurred with elagolix. Use the lowest effective dose of elagolix and is recommended. Further, patients are instructed to promptly seek medical attention in case of symptoms or signs that may reflect liver injury, such as jaundice. Patients are promptly evaluated for elevations in liver tests to determine whether the benefits of continued therapy outweigh the risks.

In the placebo-controlled clinical trials (Studies EM-1 and EM-2), dose-dependent asymptomatic elevations of serum ALT to at least 3-times the upper limit of the reference range occurred during treatment with ORILISSA (150 mg once daily—1/450, 0.2%; 200 mg twice daily—5/443, 1.1%; placebo—1/696, 0.1%). Similar increases were seen in the extension trials (Studies EM-3 and EM-4).

(e) Suicidal Ideation, Suicidal Behavior, and Exacerbation of Mood Disorders

Subjects using elagolix had a higher incidence of depression and mood changes compared to placebo, and elagolix users subjects with a history of suicidality or depression had a higher incidence of depression compared to users subjects without such a history. Patients with depressive symptoms should be evaluated to determine whether the risks of continued therapy outweigh the benefits. Patients with new or worsening depression, anxiety or other mood changes should be referred to a mental health professional, as appropriate. Patients with suicidal ideation and behavior should seek immediate medical attention. Benefits and risks of continuing elagolix should be revaluated if such events occur and optionally, elagolix should be stopped with worsening or serious depression, anxiety, mood changes or suicidal ideation.

In the placebo-controlled trials (Studies EM-1 and EM-2), elagolix was associated with adverse mood changes, particularly in those with a history of depression.

TABLE B-2

Suicidal Ideation, Suicidal Behavior and Mood Disorders in Studies EM-1 and EM-2

| Adverse Reactions | Elagolix 150 mg Once Daily (N = 475) N(%) | Elagolix 200 mg Twice Daily (N = 477) N(%) | Placebo (N = 734) N (%) |
| --- | --- | --- | --- |
| Completed Suicide | 1 (0.2) | 0 | 0 |
| Suicidal ideation | 1 (0.2) | 1 (0.2) | 0 |
| Depressed Mood, depression, depressive symptoms and or tearfulness | 13 (2.7) | 29 (6.1) | 17 (2.3) |
| Mood altered, mood swings | 25 (5.7) | 25 (5.2) | 25 (3.4) |

NOTE:
The same subject may be included in more than one row if she reported more than one adverse reaction (e.g., suicidal ideation and depression).

Example A-4: Impact of Elagolix, on Bone Turnover Markers in Women with Endometriosis-Associated Pain Who were Treated for Up to 6 Months (M) During Two, Phase 3 Studies and Did not Enroll in the Extension Studies In this study: Data were pooled from two 6M, randomized, placebo-controlled phase 3 trials (Elaris EM-I and II) evaluating two doses of elagolix (150 mg once daily [QD] and 200 mg twice daily [BID]). Women who prematurely discontinued treatment, declined to participate in, or did not qualify for the continuous use extension studies entered a Post-treatment Follow-up Period (PTFU) for up to 12M.

Materials and Methods: Participants were 18-49 year old premenopausal women with surgically diagnosed endometriosis and moderate/severe endometriosis-associated pain. The bone turnover marker serum collagen type 1 cross-linked C-telopeptide (CTx) was collected at baseline, treatment M3 and M6, and off therapy in the PTFU M3 and M6. Bone turnover collection at PTFU M12 was only required for women with the greatest bone loss. This analysis included women that had ≥one on-treatment and one PTFU value and did not enroll in the extension studies (N=296). Differences between treatment groups in mean change from baseline to each time point was analyzed using one-way ANOVA tests.

Results: Baseline CTx serum levels were similar across treatment groups. Women who received elagolix 200 mg BID had increased mean CTx serum levels at treatment M6 compared to baseline that were significantly greater than placebo (mean change from baseline[SD] pg/ml: placebo=−34.04[115.62]; 150 mg QD=5.44[148.41], p=0.177; 200 mg BID=179.16[217.79], p<0.001). Mean changes from baseline in CTx serum levels remained elevated and significantly greater than placebo off treatment through PTFU M3 in elagolix 200 mg BID (placebo=−37.29[103.98]; 150 mg QD=−9.15[156.72], p=0.180; 200 mg BID=42.64[153.37], p<0.001). Mean CTx serum levels were decreased compared to baseline at PTFU M6 across all treatment groups (placebo=−43.45[106.67]; 150 mg QD=−29.60[171.08], p=0.565; 200 mg BID=−33.33[145.60], p=0.652). Additional bone turnover markers were assessed (i.e. osteocalcin, procollagen type 1 N-terminal propeptide) and exhibited similar patterns of change as CTx.

Conclusions: In women with endometriosis-associated pain enrolled in the Elaris EM-I and II studies, treatment with elagolix 150 mg QD and 200 mg BID resulted in dose-dependent increases in mean CTx serum levels during the 6-month treatment period. CTx levels decreased after elagolix discontinuation. Similar effects would be expected in 300 QD, 300 mg BID and 600 mg QD doses.

Bone Loss

Elagolix may cause a dose-dependent decrease in bone mineral density (BMD). BMD loss is greater with increasing duration of use and may not be completely reversible after stopping treatment. The impact of these BMD decreases on long-term bone health and future fracture risk are unknown. BMD in patients should be assessed with a history of a low-trauma fracture or other risk factors for osteoporosis or bone loss. Elagolix is not recommended in women with known osteoporosis. Limit the duration of use to reduce the extent of bone loss.

Therefore, the present invention provides a method of treating endometriosis, the method comprising administering to a patient in need thereof 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof, wherein said patient experiences bone mineral density loss, wherein the bone mineral density loss is substantially reversed upon discontinuation of Compound A, or pharmaceutically acceptable salt thereof.

In yet another aspect, the present invention provides for administering to a patient in need thereof 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof, wherein said patient experiences bone mineral density loss, wherein the bone mineral density loss is substantially reversed upon discontinuation of Compound A, or pharmaceutically acceptable salt thereof.

Example A-5: Elagolix Reduces Fatigue in Patients with Moderate to Severe Endometriosis Pain A Phase III study was conducted to assess the effects of elagolix for clinically meaningful reductions in pain and other symptoms. Data provided examined the impact of elagolix on fatigue in women with moderate to severe endometriosis-related pain. In the study of three cohorts, first cohort comprised women who received placebo, second cohort comprised women who received 150 mg of Elagolix once daily and third cohort comprised women who received 200 mg of Elagolix twice daily. It is expected that 300 mg once daily or twice daily and 600 mg once daily, or similar doses will similarly show reduction in fatigue. Fatigue was assessed using the Patient Reported Outcome Measurement Information System (PROMIS®), Fatigue Short Form (SF) 6a. Six items assessed a range of self-reported symptoms from mild, subjective feelings of tiredness to overwhelming, sustained sense of exhaustion that likely decreases one's ability to execute daily activities and function normally. The domain was divided into the experience of fatigue (frequency, duration and intensity) and impact of fatigue on physical, mental and social activities. All items assessed fatigue over the previous seven days. Responses to each question was filed on a 5-item Likert scale: 1—"Not at all"; 2—"A little bit"; 3—"Somewhat"; 4—"Quite a bit"; and 5—"Very much." The questionnaire was administered at baseline and months 1, 3, and 6. Lower scores indicated less fatigue. Post-hoc, Fatigue SF-6a raw scores were converted to T-scores. The T-score rescales 5 the raw score into a standardized score such that the general population has a mean of 50 and a standard deviation (SD) of 10.

Analysis: Changes from baseline in PROMIS Fatigue SF-6a T-scores were compared between each active treatment (elagolix 150 mg QD and 200 mg BID) and placebo. 1-way Analysis of Covariance (ANCOVA) was utilized. ANCOVA controlled for treatment as main effect. Baseline Fatigue SF-6a T-score included as a covariate.

Fatigue among women with endometriosis-related pain remains an unmet medical need. At baseline, women in this study had levels of fatigue that were 1 SD worse on average than women in the general population. Compared to placebo, elagolix improved fatigue in a dose dependent manner in women with moderate to sever pain associated with endometriosis. See FIG. A-6. Statistically significant reductions relative to placebo in the PROMIS Fatigue SF-6a T-Score observed with both doses of elagolix at Months 3 and 6. A statistically significant reduction in fatigue with elagolix 200 mg was also observed as early as Month 1. See FIG. A-7. It is expected that all therapeutic doses of elagolix described above would reduced fatigue in women suffering from moderate to severe endometriosis.

METHODS OF PRACTICING THE PRESENT INVENTION

In one aspect of the invention, the methods are practiced by administering pharmaceutical compositions containing Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid. For the purposes of administration, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid may be formulated as pharmaceutical compositions. Pharmaceutical compositions comprise 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, or a pharmaceutically acceptable salt thereof, or a solvate thereof, and a pharmaceutically acceptable carrier and/or diluent. 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid is present in the composition in an amount which is effective to treat a particular disorder—that is, in an amount sufficient to achieve GnRH receptor antagonist activity, and preferably with acceptable toxicity to the patient.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. A method of managing moderate to severe pain associated with endometriosis in a premenopausal adult human female patient suffering from endometriosis and having hepatic impairment classified as Child-Pugh B, the method comprising:

providing a tablet comprising 155.2 mg or 207.0 mg of a sodium salt of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid ("elagolix sodium"), measuring hepatic function of the patient and determining that the patient has hepatic impairment classified as Child-Pugh B, orally administering the tablet comprising 155.2 mg of elagolix sodium to said patient having hepatic impairment classified as Child-Pugh B once daily for up to 6 months;

wherein said method manages the moderate to severe pain associated with endometriosis in the patient.

2. A method of managing moderate to severe pain associated with endometriosis in a premenopausal adult human female patient suffering from endometriosis and having hepatic impairment classified as Child-Pugh B, the method comprising:

oral administration of a tablet comprising 155.2 mg of a sodium salt of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid ("elagolix sodium") to the patient having hepatic impairment classified as Child-Pugh B, and continuing said oral administration to the patient having hepatic impairment classified as Child-Pugh B once daily for up to 6 months;

wherein said method manages the moderate to severe pain associated with endometriosis in the patient.

* * * * *